(12) United States Patent
Alcouloumre et al.

(10) Patent No.: US 8,118,163 B2
(45) Date of Patent: Feb. 21, 2012

(54) APPARATUS FOR SHARPS PROTECTION

(76) Inventors: Eric Alcouloumre, Laguna Beach, CA (US); Richard E. Reedy, Laguna Beach, CA (US); Jay A. Lenker, Laguna Beach, CA (US)

( * ) Notice: Subject to any disclaimer, the term of this patent is extended or adjusted under 35 U.S.C. 154(b) by 0 days.

(21) Appl. No.: 12/456,658

(22) Filed: Jun. 19, 2009

(65) Prior Publication Data

US 2009/0266729 A1     Oct. 29, 2009

Related U.S. Application Data

(63) Continuation-in-part of application No. 10/862,694, filed on Jun. 7, 2004, now abandoned.

(60) Provisional application No. 60/477,121, filed on Jun. 9, 2003.

(51) Int. Cl.
*B65D 83/10* (2006.01)
*B65D 81/26* (2006.01)

(52) U.S. Cl. ......... 206/365; 206/370; 206/523; 206/562

(58) Field of Classification Search .................. 206/366, 206/365, 562–565, 370, 63.3, 380, 523; 220/4.23, 220/359.1, 839, 359.4, 4.24, 4.22, 837
See application file for complete search history.

(56) References Cited

U.S. PATENT DOCUMENTS

| | | | |
|---|---|---|---|
| 3,861,521 A | 1/1975 | Burtz | |
| 3,944,069 A | 3/1976 | Eloridge, Jr. | |
| 4,008,802 A | 2/1977 | Freitag | |
| 4,013,109 A | 3/1977 | Sandel | |
| 4,076,882 A | 2/1978 | Fenster et al. | |
| 4,182,448 A | 1/1980 | Huck et al. | |
| 4,193,496 A * | 3/1980 | Barratt | 206/380 |
| 4,254,862 A | 3/1981 | Barratt | |
| 4,335,533 A * | 6/1982 | Kroenke | 38/141 |
| 4,373,629 A | 2/1983 | Ulin et al. | |
| 4,637,513 A | 1/1987 | Elorige, Jr. | |
| 4,671,943 A * | 6/1987 | Wahlquist | 422/300 |
| 4,674,676 A | 6/1987 | Sandel et al. | |
| 4,758,229 A | 7/1988 | Doerschner | |
| 4,859,515 A * | 8/1989 | Pothetes | 428/41.7 |
| 4,875,896 A | 10/1989 | Kurtz | |
| 4,936,449 A | 6/1990 | Conard et al. | |
| 5,024,326 A * | 6/1991 | Sandel et al. | 206/366 |
| 5,145,063 A | 9/1992 | Lee | |
| 5,161,681 A * | 11/1992 | Kemp et al. | 206/210 |
| 5,383,862 A | 1/1995 | Berndt et al. | |
| 5,385,105 A | 1/1995 | Withers et al. | |
| 5,399,169 A * | 3/1995 | Stein | 604/192 |
| D365,633 S * | 12/1995 | Walker | D24/130 |
| 5,538,132 A | 7/1996 | Propp et al. | |
| 5,570,783 A * | 11/1996 | Thorne et al. | 206/366 |
| 5,758,775 A | 6/1998 | Lowe | |
| 6,026,959 A | 2/2000 | Lowe | |
| 6,651,813 B2 * | 11/2003 | Vallans et al. | 206/366 |

* cited by examiner

*Primary Examiner* — J. Gregory Pickett
*Assistant Examiner* — Ernesto Grano

(57) ABSTRACT

Devices and methods are disclosed for protecting individuals from the sharp ends of medical objects following use on a patient. Such sharp objects include hypodermic needles, scalpel blades, cannulae, trocars, and the like. The invention utilizes a disposable protective cover for the used sharp. The protective cover is designed to surround and embed the sharp in a permanent cover that is blunt and will not permit further puncture or cutting with the sharp. In an embodiment, the protective cover also absorbs any fluids on or in the used sharp and prevents any fluids from escaping the protective cover. The sharp cover is configured to irreversibly lock, once closed. A refillable or replaceable dispenser dispenses the protective covers at points of use. A disposable receptacle receives the used sharp embedded in the protective cover. When the receptacle is full, the entire receptacle may be discarded in a medical waste container.

15 Claims, 15 Drawing Sheets

APPARATUS FOR SHARPS PROTECTION

RELATED APPLICATIONS

This application claims priority benefit from, and is a continuation-in-part of, U.S. patent application Ser. No. 10/862,694, filed on Jun. 7, 2004 now abandoned, which claims priority benefit under 35 USC §119(e) from U.S. Provisional Application No. 60/477,121, filed on Jun. 9, 2003, entitled "METHOD AND APPARATUS FOR SHARPS PROTECTION", the entirety of all of which are hereby incorporated herein by reference.

FIELD OF THE INVENTIONS

This invention relates to devices and methods to protect individuals from infectious disease spread due to puncture wounds made by sharp, contaminated objects. More particularly, the invention relates to a protective container for safely sequestering and disposing of used medical sharps.

BACKGROUND OF THE INVENTION

Pathogenic microorganisms may be present in human blood, body fluids or other infected materials and can cause infection and disease in persons who are percutaneously, or mucocutaneously, exposed. These pathogens include, but are not limited to, hepatitis B virus (HBV), hepatitis C virus (HCV) and human immunodeficiency virus (HIV). In this context, contaminated blood, body fluids or other infected materials may mean the presence or reasonably anticipated presence of pathogenic microorganisms on the surface or in a device.

A medical sharp is an object that can penetrate the skin and includes devices such as, but not limited to, needles, scalpels, tubes, wires, and other medical procedure objects, devices or instruments. Accidental puncture with contaminated, sharp needles or surgical instruments, referred to as medical sharps or sharps, remains a significant risk to healthcare workers. All healthcare workers, such as physicians, nurses, paramedics, emergency medical technicians, ambulance staff, airmedics, airmedic staff technicians, janitorial staff, office staff, and even patients and their families, are potentially at risk from this dangerous situation.

Typically, injuries resultant from accidental needle and scalpel sticks occur after the instruments have been used. As a result, healthcare workers are subject to serious diseases, including but not limited to hepatitis B virus (HBV), hepatitis C virus (HCV) and human immunodeficiency virus (HIV).

Most often, needle and scalpel punctures occur during the handling of used sharp instrumentation prior to permanent disposal. Healthcare workers can accidentally stick themselves or others in the vicinity while carrying contaminated instruments to a centrally located disposal container for used sharps. Often, needles dangerously protrude from the designated container, often located on a peripheral wall of a given room and often located behind furniture, fixtures, and medical equipment. This increases the risk of puncture to the healthcare worker placing the sharp in the container, or emptying the used sharps container.

The true cost of the problem is difficult to measure. For every "needlestick" exposure, the health care worker is subjected to batteries of tests that are repeated 3 to 4 times over the following year. If the risk is determined to be substantial, in terms of exposure to known or likely HIV, Hepatitis, or other pathogens, there may also be medication costs involved. There are side effects to medications administered for suspected disease transmission and the costs, both societal and monetary, are significant for such treatments. If a disease is actually transmitted by the event, the costs, both personal and financial, are staggering, and the event can prove to be career ending as well as adversely affecting the family and social life of the healthcare worker. Disease transmission, in the worst scenario, can be life ending for the exposed healthcare worker. Bearers of these costs, both tangible and intangible, include health care organizations, their insurers, governmental agencies, the health care workers and their families, and society as a whole.

Current solutions in the prior art include needle guards and covers, retractable needles, scalpel protectors and needleless connecting systems for intravenous solutions.

Although needle guards and covers, needles and needleless systems address part of the solution to the problem, they do not offer a universal solution that will manage the risks posed by other types of medical sharps, including scalpel blades, trocars, and the like.

The prior art includes protective devices for sharps. These are intended to enclose and blunt the used sharp, which prevents anyone from coming into contact with the contaminated sharp.

Current portable sharps containment devices accommodate needles, but may not accommodate thick sharps, such as cannulae, trocars, scalpels, hypodermic needles with an attached syringe barrel, and the like. It is generally against hospital policy and good medical practice to attempt to remove a sharp from its handle or syringe barrel because of the risk of needlestick or skin puncture and resultant contamination. Typically, sharps containment devices comprise a soft enveloping material having inadequate puncture resistance. In addition, current sharps containment devices may leak contaminated bodily fluids from the used sharp. Medical care facilities typically locate the sharps receptacle at a peripheral location within an area or room, and not at the point-of-use. There may be significant obstacles between the user and the sharps receptacle, including patient gurneys, beds, or examining tables; persons, such as patients, family members, visitors, and other health care workers; medical equipment such as IV poles and lines, monitors, wires, tubes, and other devices; or other furniture, fixtures, and equipment. This again creates the problem of the healthcare worker sticking a co-worker while moving the contaminated sharp to the disposal receptacle.

A typical sharps collector and disposal device is a mailbox-style container with or without a pull-down opening allowing access to the container. The user pulls the lid open, deposits the used sharp, and releases lid, which swings shut, much like mailing a letter. Mailbox-style containers without the pull-down opening have a tortuous path that the sharp must traverse to enter the container. The mailbox-style containers can be found in a variety of sizes and uses, such as in-hospital room containers, multi-purpose containers, mail-away containers, large volume and pharmacy containers, specialized containers, transportable containers, and the like.

A typical problem with mailbox-style receptacles is that they are frequently overfilled with needles, such that the needles stick out of the container opening. In addition, it may be difficult to put certain types of sharps, such as butterfly needles, needles attached to syringes, suture needles, trocars, cannulae, and the like, into them. An overfilled mailbox-style receptacle may result in healthcare workers becoming cut and infected by an already disposed-of sharp when they try to insert a new sharp into the receptacle and force their hand on the protruding sharp object, or by the new sharp itself. An additional risk of the mailbox-style receptacle includes the user being stuck as the sharp is being placed into the unit due to the difficulty of inserting the sharp into the tortuous pathway opening.

Not only are health care workers themselves at risk because of inadequate or unsafe disposal systems, but there are significant risks to housekeeping personnel within healthcare institutions and even to the public, who may encounter an improperly disposed, contaminated, unprotected, medical sharp device. Areas at risk include in-patient hospitals, out-patient facilities, emergency or ambulatory facilities, patient homes, offices, public restrooms, physician's offices, nursing homes, laboratories, emergency medical facilities, military facilities, helicopters, airplanes, airmedic facilities, employer facilities, hospice care facilities, needle dispensing facilities for heroin addicts and diabetics, and the like. Unprotected contaminated medical sharps are occasionally found in public areas such as public beaches, parks, and children's play areas.

New devices, procedures, systems, and methods are needed for guarding, dispensing, and collecting contaminated sharps to minimize the risk of accidental wounding of healthcare workers and others by infectious, sharp devices. Such devices and procedures are particularly important in any medical setting including in-hospital, pre-hospital, outpatient, military, and the emergency department.

SUMMARY OF THE INVENTIONS

This invention relates to devices to minimize the risk of infectious disease spread from one individual to another due to puncture wounds made by sharp, contaminated objects.

An embodiment of the invention is a guard for sharps, or a sharp guard. Another embodiment of the invention is an integrated receiver and container assembly for point-of-use medical sharps containment and disposal. In one embodiment, a solid sheet of material is bi-folded to irreversibly, seal, blunt, sequester, entrap, or render useless, medical sharps. The bi-folded sharp guard structure includes optional tabs for grasping and removal from storage as well as optional tabs that may be folded over and adhered to further secure the entrapped medical sharp. The folding tabs may further comprise incomplete labeling that becomes complete when the tabs are folded over the sequestered sharp. The complete labeling indicates the presence of an entrapped contaminated medical sharp object. In an embodiment, the sharp guard is a single use, disposable device, which is not intended to be reprocessed by cleaning, disinfection, sterilization, or the like.

In an embodiment, the sharp guard can be used at the point-of-use to protect or sequester sharp medical devices. The sharp guard may be used for most of the sharps commonly encountered in hospital, lab, ambulance, or office practice. These sharps include scalpel blades, hypodermic needles with or without an attached syringe barrel, trocars, cannulae, and the like. The sharp guard includes protection of the healthcare worker from the moment subsequent to use of a medical sharp on a patient until the point where it is physically placed in the disposal receptacle. Additionally, the sharp guard can be implemented economically using techniques such as thermoforming, injection molding, die stamping, and the like.

In one embodiment of the invention, an apparatus adapted for entrapment of medical sharps comprises a shell having an upper portion and a lower portion, an expandable hinge which connects the upper portion to the lower portion, and a pad affixed to the inside surface of the lower portion. The pad comprises an adhesive layer, and a gap-filling deformable layer disposed between the adhesive layer and the inside surface of the lower portion where a medical sharp set on the adhesive layer is trapped between the upper portion and the lower portion when the shell is closed.

In another embodiment, the apparatus adapted for entrapment of medical sharps also comprises another pad affixed to the inside surface of the upper portion. In another embodiment, a pad for entrapment of a medical sharp comprises an adhesive layer; and a gap-filling deformable layer disposed below the adhesive layer, where the gap-filling deformable layer substantially deforms to the contour of the medical sharp to fill substantially all gaps around the contour of the medical sharp when the medical sharp is pressed into the adhesive layer.

In another embodiment, a method of disposal for a used medical sharp comprises providing an open disposable sharps containment device at a point-of-use of a medical sharp, and placing the medical sharp onto the sharps containment device at the point-of-use, where the medical sharp comprises a sharp portion and a blunt portion. The method further comprises closing the sharps containment device at the point-of-use, where the sharp portion is embedded within the containment device, and the blunt portion protrudes from the closed containment device. The method further comprises transporting the containment device including the embedded medical sharp to a medical waste disposal container remotely located from the point-of-use of the medical sharp.

In a further embodiment, an apparatus adapted for entrapment of medical sharps comprises a dispenser at the point-of-use of the medical sharp, where the dispenser contains a plurality of medical sharp containment devices. Each medical sharp containment device comprises a bi-folded puncture resistant shell; and at least one adhesive pad attached to the inside of the shell. The dispenser presents the medical sharp containment device to a user for placement of a used medical sharp therein, and the dispenser presents another medical sharp containment device only upon removal of the first medical sharp containment device.

Another embodiment of the invention is a system comprising a sharp guard, a distributed sharp guard dispenser for dispensing unused sharp guards, and a sharp guard receptacle for receiving sharp guards containing a sharp.

In an embodiment, a sharp guard can be obtained from one of numerous dispensers affixed to walls or counter surfaces. The sharp guard, in another embodiment, is obtained from a transportable kit and is dispensed at the point of use. The dispensers work either manually or automatically. The sharp guard is used to safely render the sharp object unable to puncture another individual. Finally, in an embodiment, the protected sharps and sharp guard are discarded into a specially designed sharps receptacle. The sharp guard, in another embodiment, is included in prepackaged sterile surgical, suture, or procedure kits. Both the dispenser and the receptacle include optional visual monitoring, through windows or other indicators, so that the contents and fill level can be determined easily. The receptacle further includes a closure or seal for final disposal.

The sharp guard is comprised of a sheet or sheets of material that are capable of embedding, entrapping, folding over, sequestering, and otherwise rendering the sharp object harmless, unusable, and blunt. The sharp guard is, in an embodiment, a sheet of bi-folded material such as, but not limited to, cardboard, polystyrene, foamed polymer, or the like, that is folded in half over the sharp object and sealed permanently so that the sharp object cannot be removed, exposed, or otherwise used. The sharp guard includes, in an embodiment, tabs that close over the bi-folded sheet and lock or adhere to complete the closure. Labeling affixed to the surface of the sharp guard indicates when the sharp guard is undeployed, and when it is in its deployed and sealed state with biological waste entrapped therein.

In another embodiment, the sharp guard system comprises a bi-folded sheet of protective material that is presented to the medical caregiver by its dispenser. When one sharp guard is used and removed from the dispenser, another sharp guard, automatically or under manual control, is positioned for use in protecting another sharp. The medical caregiver places the contaminated sharp against the protective sheet of material and presses the sharp into the folded opening of the sharp guard and against the fold. The dispenser causes the protective cover to fold over the sharp under the influence of downward, manual pressure and coercion from side compression members on the dispenser. The protective cover finally closes and irreversibly seals over the sharp. The disabled sharp and its protective cover are removed from the dispenser and placed in a receptacle. Another sharp protective cover moves into place for ready to receive another sharp.

Materials for the protective cover for the sharp guard include, but are not limited to, foamed polymers, cardboard, polymer sheets, and the like. The internal surfaces of the sharp protective cover are preferably fabricated from adhesive materials that entrap and grab the sharp and cause the closed sharp protective cover to remain sealed over the sharp. Active foaming materials are also desirable so that the presence of the metal sharp or any liquids causes a catalytic reaction that actively foams the side of the protective cover toward the sharp and encases the sharp in foam which seals to the other side of the bi-folded protective cover or simply seals the sharp. In yet another embodiment of the invention, the fold of the bi-folded protective sheet comprises multiple creases to accommodate sharp devices of various thicknesses. Such multiple creases may comprise, for example, an accordion, "U", "Z", "V", or "W" shaped configuration.

In a preferred embodiment, the same device is used for dispensing and disposal of the Sharp Guard, and is easily, and quickly replaced when empty of new, unused product or full of used product. A user has a visual indication that the receptacle is full and that no additional sharps can be added to the receptacle. The system is foolproof and clear even to an untrained user that no additional sharps, even protected sharps, can be added. The receptacle is designed so that users can easily tell when it is full so they will not inadvertently cut themselves trying to stuff an already full container with yet another sharp. In yet another embodiment, the receptacle opening is rendered closed when it has been loaded with enough protected sharps to fill it. The sharp guard system is, preferably, a completely disposable system and is an acceptable end-receptacle for medical sharps that can be placed directly into the medical waste system without requiring an intermediate sharps container as is required by most current systems and devices. The protective covers are disposable, the dispenser is disposable, and the receptacle is disposable. All items are fabricated from materials that may be incinerated in the medical waste system.

Both the dispenser and the receptacle are preferably configured to permit access to a sharp guard with only one hand and further, to dispose of a sharp guard and entrapped sharp with only one hand. The one-handed functionality is, preferably, achieved by opening the dispenser or receptacle with only one hand and then placing the sharp guard within the receptacle, again with one hand only. This one-handed functionality relies on dispenser and receptacle opening systems that store energy and use the stored energy to open the dispenser or receptacle lid using hand or finger pressure. If the user prefers, two-handed operation is equally safe and effective.

In yet another embodiment of the sharp guard system, a healthcare provider may carry around a portable encapsulator. The portable encapsulator may be hooked to the belt, placed in a pocket, hung around the neck, etc., of the healthcare provider. The portable encapsulator comprises an openable shell, a reservoir of encapsulation material, an activation mechanism, and a hardening system. In this embodiment, the lid of the shell is opened, the sharp is placed into the shell and the lid is closed. Encapsulation material flows around the sharp and into a pre-configured mold area. The encapsulation material is then hardened to form a rigid blunt barrier around the sharp. The encapsulation system comprises material such as, but not limited to, ultra-violet (UV) curable adhesives such as those made from polyurethane, two-part epoxies, hardening foams, gels, and the like. The hardening system comprises, for example, an ultraviolet light that activates hardening of the UV curable adhesive. The key feature of this and other embodiments is that the sharp guard is available at the point-of-use.

Because the sharp guard is simple to use, there is minimal training involved and very low risk of error that could cause inadvertent injury. Its design makes it very difficult to use it incorrectly, and its correct use minimizes the risk of injury to healthcare workers. By product design, contaminated sharps are directed away from potential contact with users until the sharp is enclosed in the device. Once enclosed, accidental contact with the sharp is virtually impossible during normal use and activity. Hospital and healthcare workers can be trained and policies can be set to ensure that all workers are fully aware of the procedures necessary to make the sharp guard system functional. The implementation cost of the sharp guard system is minimal and the time to train is less than 30 minutes per trainee and, preferably, less than 10-15 minutes per trainee.

The policy to use the sharp guard comprises making the policy available on a proactive basis to all primary and ancillary personnel involved with sharps. The policy emphasizes the need to keep sharp guard systems near the point of use, including available in or around the sterile or operative field. The policy further requires that all sharps are encased or protected within a sharp guard prior to placing them in a sharps receptacle, or directly into the hospital medical waste system without an intermediate sharps receptacle. The policy preferably comprises the step of not moving your feet, as a sharps user, between when the sharp is used and when it is encased or entrapped within a sharp guard. The policy further requires that the medical sharp be encapsulated prior to turning or rotating the body when a used medical sharp is in a user's hand. Reinforcement of the policy will be an ongoing effort. The policy further comprises steps to ensure that sharp guard dispensers are maintained with unused sharp guards always available and that sharp guard receptacles never become completely full before they are emptied or disposed of. In addition, a label is preferably provided on the receptacle that indicates that the receptacle is for placement of sharp guard protected sharps only.

The sharps disposal system, in certain embodiments, can comprise a puncture resistant barrier, a fluid tight seal, an adhesive to prevent dislodgement of a used medical sharp, and a non re-openable locking system to prevent the system from being re-opened. The sharps disposal system advantageously comprises a low-cost liner that serves as an enhanced puncture barrier. The foam is capable of absorbing liquids and of sealing the perimeter of the sharp disposal system in its closed configuration. As such, the sharps disposal system is portable and available at the point of use in the medical environment, but meets all requirements for final disposal of medical sharps so that use of a secondary, sharps disposal container is not required prior to placement of the entrapped medical sharp within the red biohazard bag within the medical facility. These requirements include stability, durability, resistance to puncture, resistance to impact, resistance to leakage of contaminated biological fluids and tissues during use, handling, storage, and transportation. The sharps disposal is convenient and accessible to medical caregivers and to those who use, maintain, and dispose of medical sharp devices. Furthermore the system can comprise a closure device design to minimize exposure to sharps during activation and designed to resist manual opening once sharps are enclosed therein. The sharps disposal container can comprise a receiving pad further including one or more needle re-capping feature, a sharp safety zone, and a suture needle collection and counting area. The entire system is configured for assembly line manufacturing at very low cost to enable its use on a widespread basis in a wide variety of medical venues.

In an embodiment, when a specific medical sharp has been identified as suitable for point-of-use disposal, a sharp guard can be functionally and physically tailored for this application. The sharp guard is preferably configured or fabricated to hold the sharp securely, and entirely entrapped, for disposal. The embodiment may use all of some of the typical sharp guard features of protective exterior shell, absorbent foam, mat liners, adhesives and clasp and interlock closures. The sharp may be pre-packaged in the sharp guard and when used, disposed of in the same container. This provides all of the advantages discussed elsewhere of the sharp guard disposal system. Sharp guard applications include supporting many outpatient or home health care recurring injections.

In other embodiments, the Sharp guard can comprise permanent or temporary adhesives, clamps, or high-friction materials or structures on its bottom surface to resist sliding relative to a surface on which it rests. It is beneficial that the Sharp guard not slide or easily move around relative to the surface on which it rests so that a user can insert contaminated medical sharps with one hand and the Sharp guard does not slide or move inappropriately under the manually applied forces. Such adhesives can comprise partially or fully cross-linked adhesives, hook and loop fasteners, double-sided adhesive tape, clips, clamps, buttons, snaps, or the like.

In other embodiments, the Sharp guard can comprise a strap, belt, or other closure capable of being wrapped around protruding blunt ends of entrapped sharps such that the medical sharp is fully prevented from backing out of an opening in the Sharp guard. The strap, belt, or other closure can be affixed to the bottom of the shell and be selectively affixed to the top of the shell using irreversible or reversible fasteners.

In other embodiments, the Sharp guard can comprise labeled regions on one of the internal foam pads or adhesive layers that indicate appropriate areas in which to insert the pointed part of the medical sharp so that removal forces of the medical sharp exceed specified values.

In some embodiments, the Sharp guard can be used to entrap, sequester, embed, hold, or otherwise convey a used, contaminated medical sharp from the point of use directly into the biohazard disposal bag commonly found in medical facilities. In these embodiments, the wall-mounted hard, sharps disposal containers are not required for intermediate placement of the contaminated medical sharps prior to disposal in the biohazard waste. The biohazard waste, or biohazard trash, is generally a polymeric bag and is generally colored red to signify the presence of a hospital biohazard. This biohazard bag is often termed the "red bag". Typically, biohazard waste is disposed in an incinerator.

In other embodiments, the Sharp guard can comprise internal high-friction materials to minimize the risk of the entrapped medical sharp moving once placed therein. Such high-friction materials can comprise top or bottom foam pads or other structures exposed therein.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTIONS

In accordance with one or more embodiments of the present invention, a plurality of embodiments of a sharp guard system is described herein. In order to fully specify this preferred design, various embodiment specific details are set forth, such as the shape and size of the receptacle as well as the dispenser. It should be understood, however that these details are provided only to illustrate the presented embodiments, and are not intended to limit the scope of the present invention.

Figure 1A:
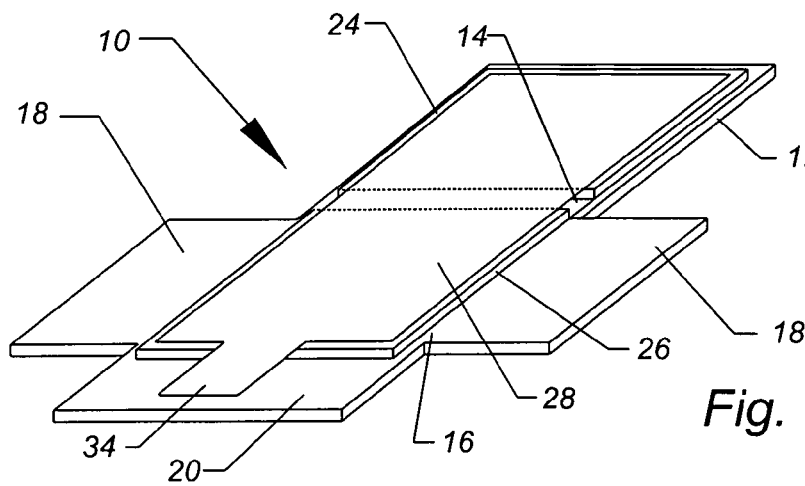
FIG. 1A illustrates an oblique view of a flat, un-deployed sharp guard, according to an embodiment of the invention.

FIG. 1A illustrates an oblique view of an embodiment of a sharp guard 10 in the fully open or flat configuration. The sharp guard 10 comprises an upper support 12, a hinge area 14, a lower support 16, a plurality of optional folding tabs 18, and a pull-tab 20. The upper support 12, the hinge area 14, the lower support 16, the optional folding tabs 18 and the pull-tab 20 of the sharp guard 10 are permanently affixed to each other and are, preferably, fabricated from the same piece of material in a unitary structure. In some embodiments, the hinge area 14 is pre-defined and located at a specific location on the lower support 16, the upper support 12, or both.

In an embodiment, the upper support 12, the hinge area 14, the lower support 16, the optional folding tabs 18 and the pull-tab 20 are fabricated from puncture resistant thermoplastic materials including, but not limited to, polyethylene terephthalate, polystyrene, polyethylene, polypropylene, or the like.

In another embodiment, other puncture resistant materials, including, but not limited to, cardboard, paper, polyurethane foam, polyvinyl chloride foam, cork, synthetic composites, polyester, and the like, may be used. Because of its minimal cost and easy manufacturability, polystyrene sheet is the preferred material for fabrication of the upper support 12 and the lower support 16, including any tabs 18.

In another embodiment, the upper support 12, the hinge area 14, the lower support 16, the optional folding tabs 18 and the pull-tab 20 are laminated with puncture resistant materials, such as ceramics, metals, or polymers. Exemplary laminate materials include, but are not limited to, low density polyethylene, polyester, polyimide, polyamides, stainless steel, stainless steel mesh, Kevlar®, aluminum, and the like.

Fabrication processes for upper support 12, the hinge area 14, the lower support 16, the optional folding tabs 18 and the pull-tab 20 include, but are not limited to, extrusion, injection molding, insert molding, thermoforming, and the like.

The sharp guard 10 further comprises an upper adhesive region 24 and a lower adhesive region 26. The upper and lower adhesive regions 24 and 26, respectively, are permanently adhered to the upper support 12 and the lower support 16 and comprise an embedding adhesive material. The upper adhesive region 24 and the lower adhesive region 26 are configured to permanently and irreversibly bond to each other and entrap or sequester the sharp therein when the sharp guard 10 is folded closed over a sharp. Further, the embedding adhesive of the upper adhesive region 24 and the lower adhesive region 26 not only sticks to itself and an entrapped sharp, but deforms and completely conforms to and surrounds the sharp. The adhesive is malleable and deforms to surround and fill any gaps or spaces that may be created around a large diameter sharp. The adhesive regions 24 and 26 preferably do not extend into the hinge area 14. The gap-filling nature maximizes adhesive contact surface area on the sharp and seals the sharp to prevent fluid leakage or spillage.

In an embodiment, the upper adhesive region 24 and the lower adhesive region 26 are thick and flowably or malleably deformable. Thus, when a thick sharp is enclosed within the sharp guard 10, the adhesive regions 24 and 26 flow aside and permit full entrapment of the large sharp with no air gaps extending to the exterior of the upper support 12 or lower support 16.

Further, such prevention or minimization of air gaps will prevent smaller sharps that are placed within the sharp guard 10 from inadvertently falling out through the air gap route to the exterior of the sharp guard 10.

The upper adhesive region 24 and the lower adhesive region 26 are fabricated from adhesives that permanently adhere to the upper support 12 and the lower support 16, respectively. Examples of the embedding adhesive utilize or comprise base materials of acrylics, acrylate polymers, polychloroprenes, cyanoacrylates, and the like. In an embodiment, the upper adhesive region 24 and the lower adhesive region 26 are approximately 0.01 inch to approximately 2.0 inches thick, and preferably 0.1 inch to approximately 0.5 inch thick.

In another embodiment, the embedding adhesive is laminated onto foam, which is preferably malleably deformable to accommodate sharps of varying size and thickness. This is to enhance bond strength, which is dependent upon the amount of adhesive-to-surface contact developed. Examples of the foam are closed cell polyvinyl chloride foam (vinyls), styrene block copolymer (SBC), polyurethane, polyester, open cell polyvinyl chloride foam (vinyls), styrene block copolymer (SBC), and the like. In an embodiment, the foam is approximately 0.1 inch to approximately 2.0 inches thick, and preferably 0.25 inch to approximately 1.5 inches thick.

In another embodiment, the embedding adhesive is laminated onto a gel, which is preferably malleably deformable to accommodate sharps of varying size and thickness. Examples of the gel are sealant type materials utilizing a base material of epoxy, acrylic, nitrile, hydrophilic hydrogel, collagen, and the like. In an embodiment, the gel is approximately 0.1 inch to approximately 2.0 inches thick, and preferably 0.25 inch to approximately 1.5 inches thick.

In yet another embodiment, the adhesive, gel or foam is affixed only at or near the exterior of the sharp guard 10 to prevent exit routes for the sharps while maintaining a lower overall device cost.

In another embodiment, the upper adhesive region 24 and the lower adhesive region 26 comprise an absorbent material, such as, but not limited to, carboxymethyl cellulose, cotton, paper, sea sponge, hydrophilic hydrogel, wood cellulose fiber, cellulose-based fiber granules, absorbent polyacrylate, wood pulp/polypropylene/cellulose, wood pulp and other fiber blends with polypropylene, polyester and polyethylene, and the like. In addition, specialized absorbent and foaming materials such as, but not limited to, encapsulated monosodium citrate and an alkali metal or alkaline earth metal salt thereof could also be utilized. Specific applications may contain any combination of components such as carboxy-methyl cellulose, polypropylene, non-woven polyethylene film laminate, cellulose/polyester, non-woven polyester microfiber, polyethylene coated film or paper and polyester packing pouches.

The sharp guard 10 further comprises an adhesive cover strip 28 on the exposed surface of the adhesive regions 24 and 26. The adhesive cover strip 28 further comprises an adhesive cover strip pull-tab 34. The adhesive cover strip 28 and its integral adhesive cover strip pull-tab 34 cover the adhesive regions 24 and 26 until such time as the adhesive cover strip 28 is removed and the sharp guard 10 is ready for a medical sharp object to be adhered and sandwiched between the upper adhesive region 24 and the lower adhesive region 26. The adhesive cover strip pull-tab 34 is designed to facilitate easy grasping by the user and enables the user to lift the adhesive cover strip 28 to fully uncover the adhesive regions 24 and 26. It is preferable that the adhesive cover strip 28 be removed from both the upper adhesive region 24 and the lower adhesive region 26 using a single motion on the part of the user. Thus, in an embodiment, a single pull-tab 34 controls the cover strips 28 over both the upper adhesive 24 and the lower adhesive 26.

The adhesive cover strip 28 and the adhesive cover strip pull-tab 34 are preferably a unitary structure and comprise materials that do not adhere to the upper adhesive region 24 and the lower adhesive region 26. Such materials depend on the nature of the embedding adhesive material used in the upper adhesive region 24 and the lower adhesive region 26. In an embodiment, polytetrafluoroethylene, other fluoropolymers, metal foils, and the like, are suitable materials for the adhesive cover strip 28 and the adhesive cover strip pull-tab 34.

The pull-tab 20 is designed to facilitate easy grasping of the sharp guard 10 by the user and enables the user to remove the sharp guard 10 from a sharp guard dispenser.

The flat configuration illustrated in FIG. 1A is the configuration in which the sharp guard 10 is manufactured and most compactly stored prior to use. The sharp guard is sized so that it can encapsulate the majority of medical sharps. In an embodiment, the length of the sharp guard 10 from the upper support 12 to the tab 20 is between approximately 0.5 inch and approximately 10 inches, preferably is between approximately 2 inches and approximately 7 inches and most preferably is between approximately 3 inches and approximately 5 inches. In an embodiment, the width of the sharp guard 10 from an outside edge of one tab 18 to an outside edge of an opposite tab 18 is between approximately 0.5 inch and approximately 10 inches, preferably is between approximately 2 inches and approximately 7 inches and most preferably is between approximately 3 inches and approximately 5 inches.

Figure 1B:
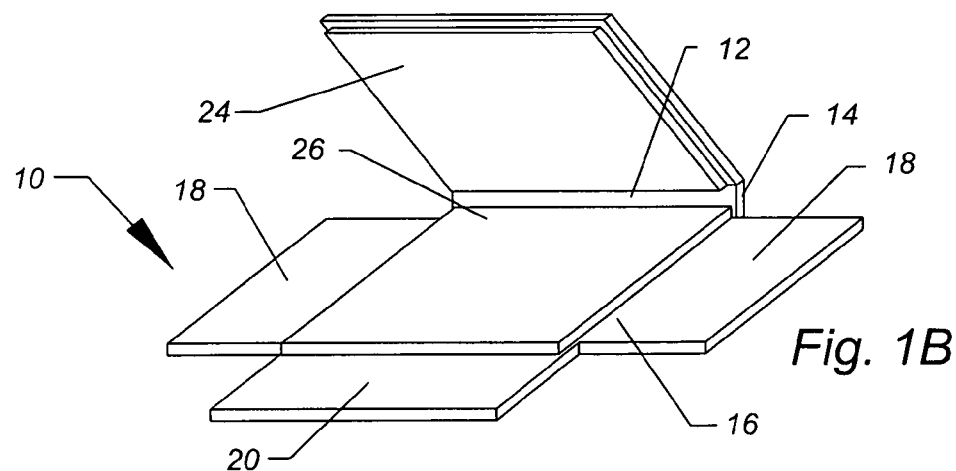
FIG. 1B illustrates an oblique view of the sharp guard in its open, deployed state, according to an embodiment of the invention.

FIG. 1B illustrates an oblique view of an embodiment of the sharp guard 10 in a partially folded and partially open configuration. The sharp guard 10 comprises the upper support 12, the hinge area 14, the lower support 16, optional folding tabs 18, and the pull-tab 20.

In an embodiment, the hinge area 14 is integrated with the upper support 12 and the lower support 14, and is height adjustable. The hinge area 14 is height adjustable to permit the sharp guard 10 to accommodate sharps of varying thickness. Typically, a medical sharp comprises a sharp portion connected to a blunt portion. Sharp portions are, for example, needles, scalpel blades, trocars, tubes, wires and other medical procedure devices, objects or instruments, which can penetrate the skin, and the like. Blunt portions are, for example, handles, syringe bodies, tubing, connectors, catheters, specialized containers, and the like. Typically, once used, the entire medical sharp is thrown away.

The hinge area 14 is preferably fabricated by creating creases or thin areas in the upper support 12 and the lower support 14, which are, preferably, fabricated from the same piece of material. In an embodiment, the hinge area 14 comprises a complex hinge or multiple hinges. In an embodiment, the hinge area 14 comprises a single crease or region of material thinness. In another embodiment, the hinge area 14 is a doubly creased area forming a "U" shape or a book hinge. In a further embodiment, the hinge area 14 is a "W" folded or tri-folded configuration capable of expanding substantially. In another embodiment, the hinge area 14 is an accordion fold or z-fold that comprises a plurality of hinges to allow the hinge area 14 to expand substantially or compress substantially. Since the thickness of a sharp to be embedded is variable, the hinge 14 accommodates a wide range of thicknesses and still allows the upper support 12 and the lower support 16 to be substantially parallel to each other when the sharp guard 10 is closed around the sharp. The accordion fold or other multiply creased hinge 14 provides for such parallelism in the closure of the upper support 12 and the lower support 16.

In an embodiment, the thickness of the folded, unexpanded hinge area 14 is between approximately 0.1 inch and 0.25 inch. When expanded, the hinge 14 is between approximately 0.1 inch and 2 inches, and preferably is between 0.25 inch and 1.5 inches.

Figure 1C:
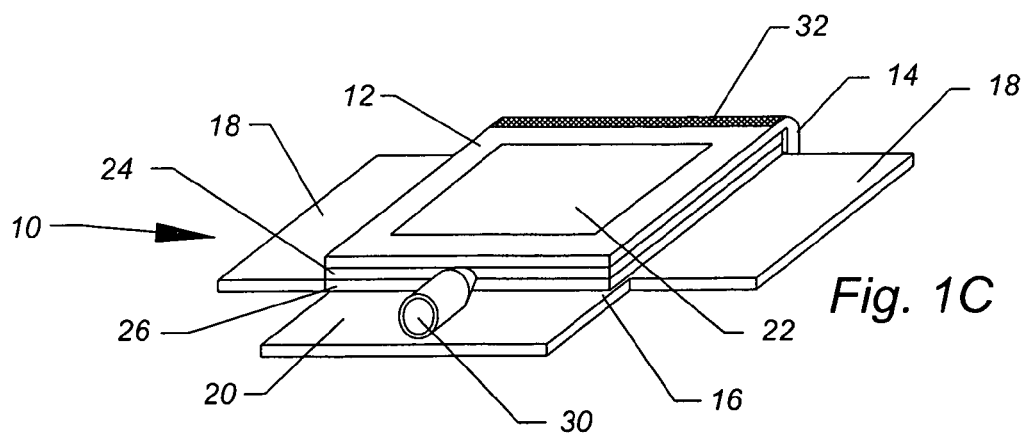
FIG. 1C illustrates an oblique view of the sharp guard in the closed state with a hypodermic needle trapped therein, according to an embodiment of the invention.

FIG. 1C illustrates an oblique view of an embodiment of the sharp guard 10 in a closed configuration with a sharp medical object 30 embedded therein. Typically, a healthcare worker places the used medical sharp 30 into the lower adhesive region 26 and folds the upper support 12 over the lower support 16. The upper adhesive region 24 and the lower adhesive region 26 adhere together, embedding the sharp 30. The upper support 12, the hinge area 14, and the lower support 16 form a puncture resistant shell or case around the embedded sharp 30.

In an embodiment, the health care worker can also fold the optional tabs 18 over the upper support 12 to provide additional sealing of the sharp guard 10.

In an embodiment, the optional tabs 18 comprise snaps or locks to provide audible and tactile feedback that the sharp guard 10 is closed around the sharp. The snaps or locks preferably irreversibly lock the sharp guard 10 closed. These locks may be molded into the structure and comprise tapers that facilitate intermeshing of the sharp guard 10 surfaces and overhangs or catches that prevent disengagement of the locked sharp guard 10.

Thus, the sharp guard 10 protects the healthcare worker from needlesticks, punctures, and cuts caused by the contaminated sharp 30. The sharp guard 10 is applied to the contaminated sharp 30 at the point of use, which may, in an embodiment, generally be described as a location wherein the user does not have to move their feet or turn to apply the sharp guard 10 to the contaminated sharp 30.

The sharp guard 10 further comprises a label 22. The label 22 preferably comprises a standard biohazard symbol and a notation that the contents may be pathogenic or contaminated with medical waste. In one embodiment, the label 22 is affixed to the outer surface of the upper support 12. In yet another embodiment, the label 22 affixed to the underside of the plurality of optional folding tabs 18 so that when the tabs are folded over the upper support 12, their edges are adjacent and a complete statement is legible. When the tabs 18 are open, the part of the label 22 on each tab 18 is incomplete and does not display a coherent message. In an embodiment, the lower adhesive area 26 extends onto the upper surfaces of the tabs 18 and serves as a permanent and irreversible closure for the tabs 18 when they are folded over the outside of the upper support 12.

The sharp guard 10, in another embodiment, further comprises an adhesive catalyst 32. In an embodiment, the adhesive catalyst 32 is located on the outer surface proximate to the hinge area 14. In another embodiment, the adhesive catalyst 32 is proximate to and over the hinge area 14. The adhesive catalyst 32 promotes adhesion between the employed sharp guard 10 and a sharp guard receptacle when the employed sharp guard 10 is placed in the sharp guard receptacle.

Figure 2A:
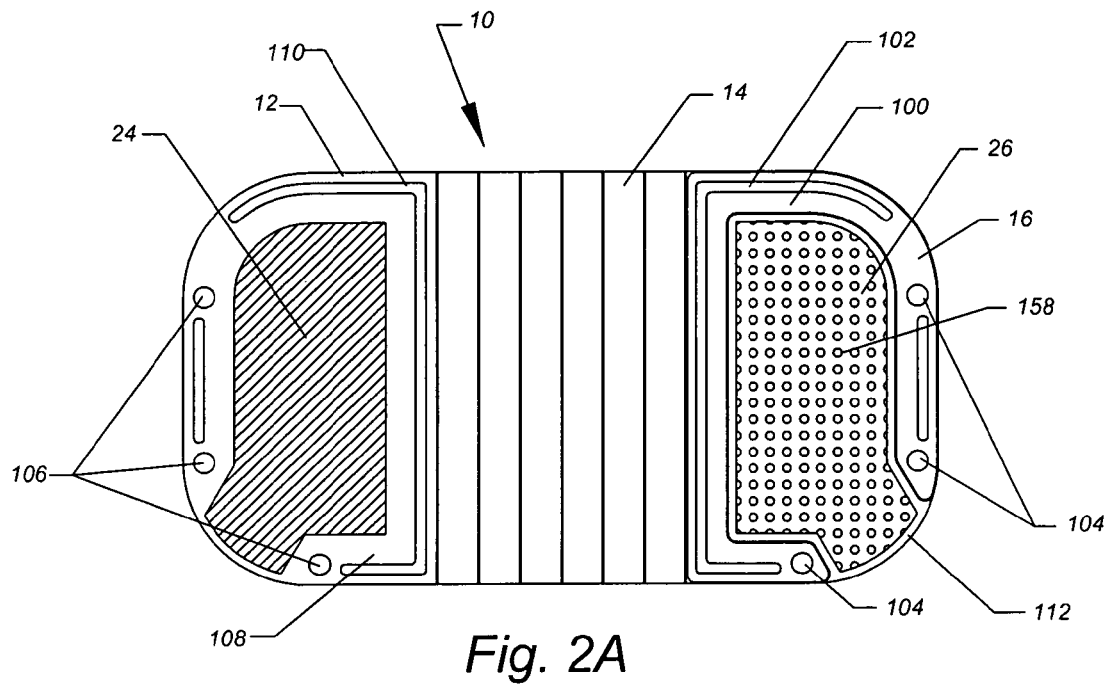
FIG. 2A illustrates a top view of the sharp guard in its undeployed flat configuration, according to another embodiment of the invention.

FIG. 2A illustrates another embodiment of the sharp guard 10. The sharp guard 10 comprises the upper support 12, the hinge area 14, and the lower support 16. The upper support 12 further comprises a plurality of protrusions 106, and a flat area 108 having an optional raised stiffening rim 110. The raised rim 110 is slightly raised to maximize structural stiffness and rigidity. The lower support 16 further comprises a plurality of circular depressions 104, and a raised area 100 having an optional recess 102.

The protrusions 106 and the raised stiffening rim 110 on the upper support 12 are aligned with the circular depressions 104 and the recess 102 on the lower support 16 such that when the sharp guard 10 is folded over the sharp 30, the protrusions 106 and the raised stiffening rim 110 fit snugly within and intermesh with the circular depressions 104 and the recess 102, respectively. In an embodiment, the protrusions 106 latch into the depressions 104 when the sharp guard 10 is closed. In an embodiment, the protrusions irreversibly 106 latch into the depressions 104 when the sharp guard 10 is closed.

In another embodiment, the flat area 108 comprises slots, wells, or cutouts that accept the raised area 100 and permit the raised area 100 to project beyond the plane of the flat area 108 of the bi-folded surfaces.

The sharp guard 10 further comprises the upper adhesive region 24 and the lower adhesive region 26. The upper adhesive region 24 is level with the flat area 108. The lower adhesive region 26 sets in a depression surrounded by the raised area 100. In an embodiment, the upper adhesive region 12 and the lower adhesive region 16 comprise an embedding adhesive material such as polyurethane-based adhesives, acrylics, acrylate polymers, polychoroprenes, cyanoacrylates, and the like. The lower adhesive region 26 optionally comprises holes, openings, or fenestrations 158 which permit diffusion or absorption of fluid from the embedded sharp 30 into a region separated from the sharp 30 by the lower adhesive region 26.

In an embodiment, the lower adhesive region 26 further comprises an absorbent spun material, such as, for example compounds of methyl cellulose, cotton, paper, polyester, polypropylene non-woven/polyethylene film laminate, cellulose/polyester, non-woven polyester microfiber, polyethylene coated film or paper, polyester packing pouches, and the like, under the embedding adhesive material. In another embodiment, the spun material comprises absorbent additives, such as, for example, carboxymethyl cellulose, hydrophilic hydrogel, sea sponge, wood cellulose fiber, cellulosic-based fiber granules, absorbent polyacrylate, wood pulp/polypropylene/cellulose, wood pulp and other fiber blends with polypropylene, polyester and polyethylene, and the like. In addition, special absorbent materials may be added such as, but not limited to, encapsulated monosodium citrate and an alkali metal or alkaline earth metal salt thereof and the like. In an embodiment, the upper adhesive region 24 and the lower adhesive region 26 further comprise the absorbent spun material.

In yet another embodiment, the lower adhesive region 26 further comprises a foaming material, such as, but not limited to, encapsulated monosodium citrate and an alkali metal or alkaline earth metal salt thereof, and the like, under the embedding adhesive material. The foaming material foams in the presence of the metal sharp 30 or any liquids present with the used metal sharp 30, to further contain the used sharp 30. In another embodiment, the upper adhesive region 24 and the lower adhesive region 26 further comprise the foaming material.

In yet another embodiment, the lower adhesive region 26 further comprises a cover. The cover facilitates contact with the deformable and/or absorptive material of the upper and/or lower adhesive regions 24, 26. In an embodiment, the cover may be treated with an adhesive. In an embodiment, the cover material may be a fine denier woven or non-woven spinable polyester. In yet another embodiment, the upper adhesive region 24 and the lower adhesive region 26 further comprise the cover.

In another embodiment, the sharp guard 10 further comprises a lower opening 112. The lower opening 112 is located along an edge of the lower support 16 at a break in the raised area 100. The lower adhesive region 26 extends into the lower opening 112. The upper adhesive region 24 extends into the flat area 108. The lower opening 112 and the upper adhesive region 24 which extends into the flat area 108 are aligned such that the upper adhesive region 24 which extends into the flat area 108 sets over the lower opening 112 when the user closes the sharp guard 10.

Figure 2B:
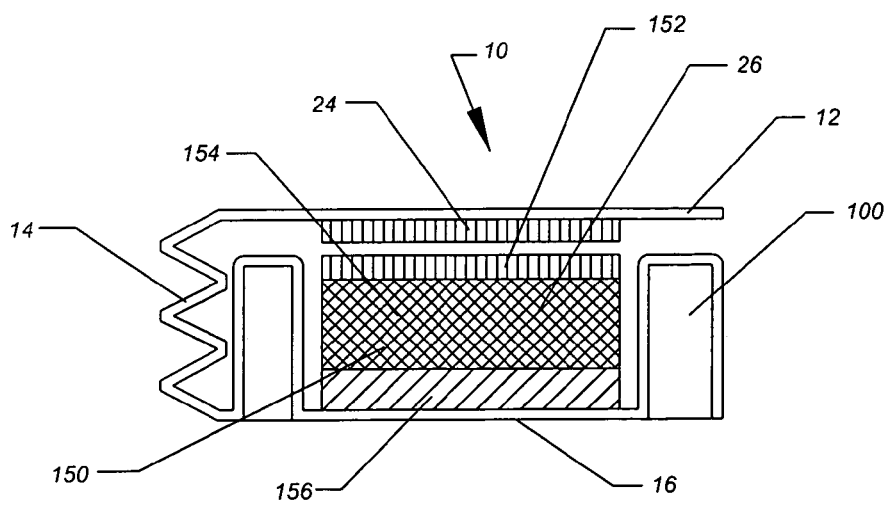
FIG. 2B illustrates a side cutaway view of a folded sharp guard showing additional details of an entrapment pad, according to an embodiment of the invention.

In another embodiment, the lower adhesive region 26 comprises a pad 150. FIG. 2B illustrates a cross section of the sharp guard 10 comprising the pad 150. The pad 150 comprises an adhesive layer 152 comprising materials such as acrylics, acrylate polymers, polychloroprenes, cyanoacrylates, and the like. The adhesive layer 152 adheres to the sharp 30, the upper adhesive region 24, and itself when the sharp guard 10 is closed around the sharp 30 to embed and entrap the sharp 30 within the sharp guard 10.

In another embodiment the pad 150 further comprises a gap-filling deformable layer 154 disposed between the adhesive layer 152 and an inside surface of the lower support 16. Examples of a gap-filling deformable material include, but are not limited to hydrogel, soft foams of polyvinyl chloride, polyurethane, or polyester, closed cell polyvinyl chloride foams (vinyls), polystyrenes, styrene block copolymer (SBC), polyurethanes, polyesters, or the like. The gap-filling deformable layer 154 deforms when the sharp 30 is embedded or pressed into the pad 150 to substantially fill any gaps surrounding the sharp 30. The deformation is either resilient or the result of irreversible crushing of the gap-filling material. This further contains sharps 30 of varying sizes and diameters within the sharp guard 10 when the sharp guard 10 is closed. The gap-filling deformable layer 154 expands to fill an interior space of the closed sharp guard 10 having the embedded sharp 30 such that there are substantially no gaps in the closed, employed sharp guard 10.

In an embodiment, the pad 150 further comprises an absorbent layer 156 disposed below the adhesive layer 152, comprising materials such as, for example, wood cellulose fiber, cellulose-based fiber granules, absorbent polyacrylate, wood pulp/polypropylene/cellulose, wood pulp, or the like. In another embodiment, the pad 150 comprises a composite, an integrally distributed, or an itemized absorbent material, such as, for example, particles of carboxymethyl cellulose suspended in open-celled polyurethane foam, air-laid paper, wood cellulose fiber, cellulose-based fiber granules, absorbent polyacrylate, wood pulp/polypropylene/cellulose, wood pulp and other fiber blends with polypropylene, polyester and polyethylene, or the like. The absorbent layer 156 or the absorbent materials substantially absorb any fluids contained on and/or in the used sharp 30 to prevent fluids from leaking from the closed sharp guard 10. The adhesive layer 152, in an embodiment, is perforated or fenestrated with openings 158 to permit fluid flow or diffusion into the layers below.

In another embodiment, the upper adhesive region 24 comprises the pad 150. In a further embodiment, the upper adhesive region 24 and the lower adhesive region 26 each comprise the pad 150.

In an embodiment, the sharp guard 10 has a orientation edge or guide to assist the healthcare professional with proper alignment of a syringe body and other pharmaceutical injection or infusion devices into the sharp guard 10. This ensures that needles, catheters and other elongated medical sharps are properly orientated for maximum containment with the sharp guard 10.

The raised area 100 forms a raised ridge with respect to the lower adhesive region 26 to prevent the sharp from inadvertently being poked out of the edge of the sharp guard 10. The ridge or raised edge forms a material barrier to the sharp 30 around much of the perimeter of the folded sharp guard 10. The ridge or raised edge preferably does not extend through the lower opening 112 where the medical sharp 30 is inserted and a handle or other blunt portion may project out of the sharp guard 10. This is especially useful in the context of large syringes or scalpels. The intermeshing of the raised rim 110 and protrusions 106 with the recess 102 and the depressions 104 provides a barrier against sharps penetration.

Referring to FIG. 2A, the hinge area 14 is preferably fabricated by creating creases or thin areas in the upper support 12 and the lower support 16, which are, preferably, fabricated from the same piece of material. In an embodiment, the hinge area 14 is an accordion fold that comprises a plurality of hinges to allow the hinge area 14 to expand substantially or compress substantially. Since the thickness of the sharp 30 to be embedded is variable, the hinge 14 accommodates a wide range of thicknesses and still allows the upper support 12 and the lower support 16 to be substantially parallel to each other when the sharp guard 10 is closed around the sharp 30. The accordion fold or other multiply creased hinge area 14 provides for such parallelism in the closure of the upper support 12 and the lower support 16.

In an embodiment, the thickness of the hinge area 14 is between approximately 0.1 inch and 0.25 inch. When expanded, the thickness of the hinge area 14 is between approximately 0.1 inch and 2 inches, and preferably is between 0.25 inch and 1.5 inches.

In another embodiment of the sharp guard 10, a pouch fabricated from materials including, but not limited to, Tyvek®, polyethylene, polypropylene, or the like is heat sealed around the sharp guard 10 and the sharp guard 10 is sterilized using ethylene oxide, gamma irradiation, or the like. The sharp guards 10 are preferably separately bagged or pouched and irradiated for single use in a sterile environment. In an embodiment, the pouch is a typical heat-sealed chevron-style or other style pouch known in the art as aseptic packaging that may be opened and the sterile sharp guard 10 contents spilled or dumped into the sterile field using aseptic procedure. By this method, the sharp guards 10 may be deployed onto a sterile field for use when needed.

In yet another embodiment, the sharp guards 10 are double pouched in a manner known as double aseptic packaging. A double-pouched sharp guard is a sterile safeguard 10 pouched in a first sterile pouch, and then the pouched safe guard 10 is pouched in a second sterile pouch.

Figure 3:
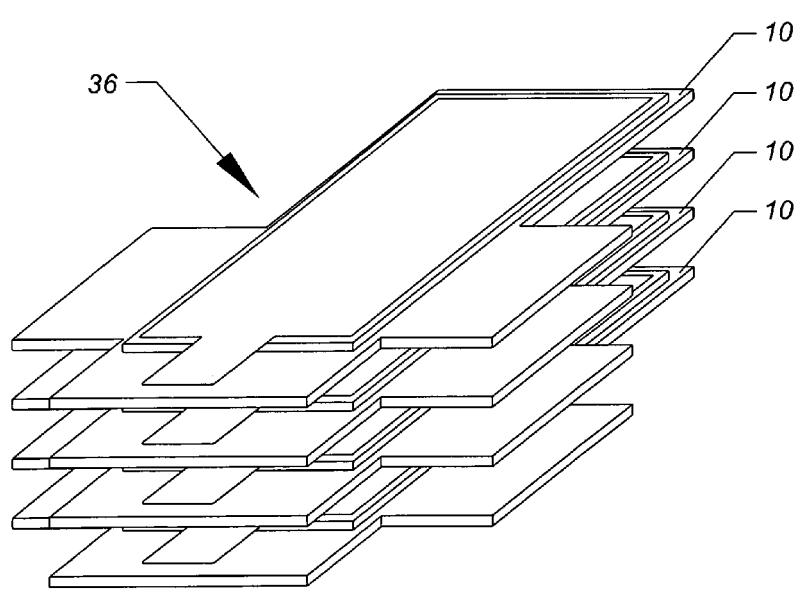
FIG. 3 illustrates an oblique view of a stack or plurality of un-deployed, flat sharp guards, according to an embodiment of the invention.

FIG. 3 illustrates an oblique view of a stack 36 sharp guards 10. In an embodiment, the stack 36 comprises between 1 and 100 sharp guards 10. In another embodiment, the stack 36 comprises between 5 and 50 sharp guards 10, and in yet another embodiment, the stack 36 comprises between 10 and 30 sharp guards 10. In a further embodiment, the stack 36 comprises more than 100 sharp guards 10. The stack 36 facilitates shipping, storage, and dispensing of the sharp guards 10. The sharp guards 10 may be non-sterile or they may be bagged or pouched and sterile.

Figure 4A:
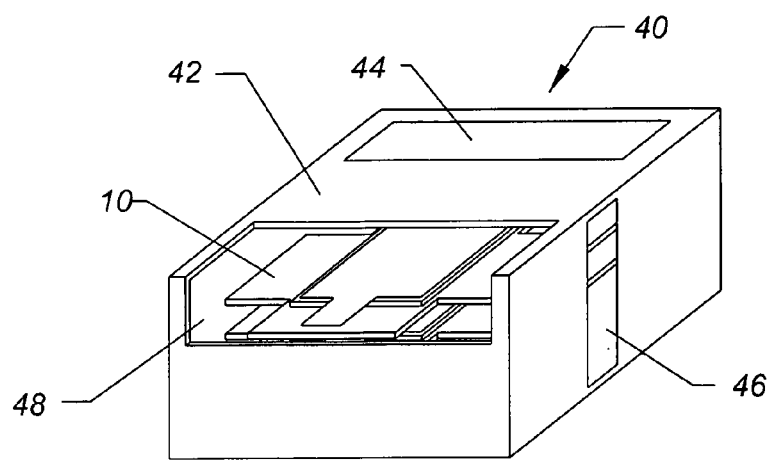
FIG. 4A illustrates an oblique view of a sharp guard dispenser with a plurality of un-deployed sharp guards loaded therein, according to an embodiment of the invention.

FIG. 4A illustrates an oblique view of a dispenser 40 for sharp guards 10. The dispenser 40 comprises a case 42, a mount 44, a window 46, and an opening 48. The dispenser 40 is loaded with a plurality of sharp guards 10.

The mount 44 is affixed to the case 42 and is used to removably affix the case 42 to another object such as a table, bed, wall, or the like. The window 46 is affixed to the case 42 and permits viewing of the sharp guards 10 or other contents of the case 42. The opening 48 is a penetration through the case 42 and may be located on the front of the case 42, on the top of the case 42, or it may be positioned partially on the top and partially on the front of the case 42, as shown in FIG. 4A.

In an embodiment, the case 42 of the dispenser 40 is fabricated from materials such as, but not limited to, polyvinyl chloride, polyethylene, polypropylene, polyester terephthalate (PET), acrylonitrile butadiene styrene (ABS), polystyrene, copolymers of the aforementioned, metal, sealed wood, cardboard, or any other material suitable for a container. In an embodiment, the preferred material is PET, cardboard, or polystyrene because of the low manufacturing cost of these materials. Preferred manufacturing methods for the case 42 include, but are not limited to, lamination, blow molding, extrusion, injection molding, thermoforming, and the like.

The mount 44 comprises non-permanent adhesives, magnets, clips, clamps, or the like. The mount 44 is configured to allow the case 42 to be mounted to a wall, tabletop, bed rail, or any other surface or structure commonly found in a hospital, ambulance, or other medical facility.

Figure 4B:
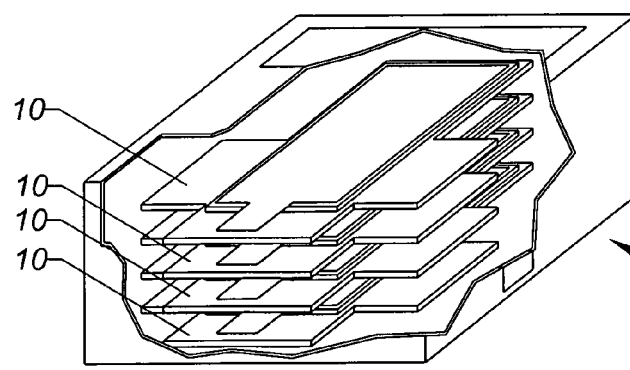
FIG. 4B illustrates an oblique cut away view of the sharp guard dispenser filled with a plurality of un-deployed sharp guards, according to an embodiment of the invention.

FIG. 4B illustrates a cut-away image of an oblique view of the dispenser 40. The dispenser 40 comprises a plurality of sharp guards 10. Referring to FIGS. 3 and 4B, the sharp guards 10 are arranged in the stack 36. The sharp guards 10 in the stack 36 may be sterile and separately pouched or they may be non-sterile. In an embodiment, the sharp guards 10 are labeled with full Food and Drug Administration (FDA), Occupational Safety and Health Administration (OSHA) and International Standards Organization (ISO) specified labeling to characterize the device and the sterile or non-sterile nature of the device.

Figure 4C:
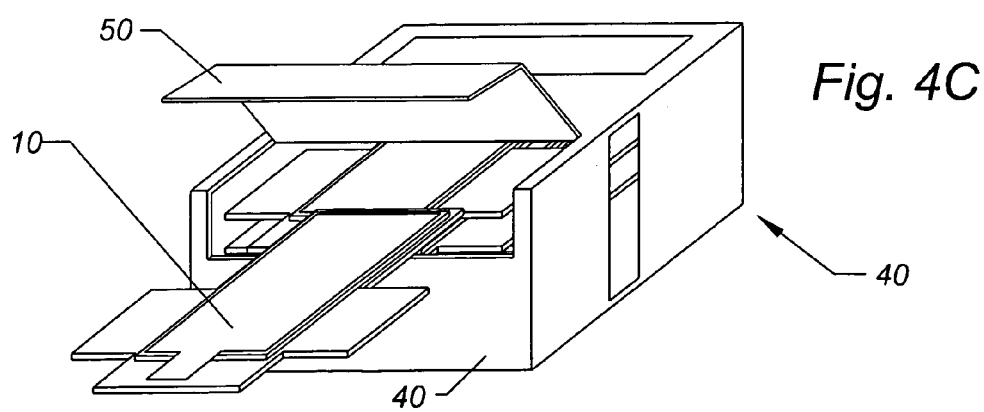
FIG. 4C illustrates an oblique view of the sharp guard dispenser with a sharp guard being removed, according to an embodiment of the invention.

FIG. 4C illustrates an oblique view of the dispenser 40 with the sharp guard 10 being removed through the opening 48. The dispenser 10 further comprises an optional lid closure 50. The lid closure 50 is hinged to the case 42 so that it may be opened and closed. The lid closure 50 further comprises an optional lock to hold the lid closure 50 closed against the case 42. In an embodiment, the lid closure 50 comprises a spring to bias the lid closure 50 in the open position. The lock holding the lid closure 50 closed comprises a release button that may be depressed with a single finger. Depressing the lock releases the lid closure 50 and the spring causes the lid closure 50 to open, thus the lid closure 50 is operable with a single press of the hand or finger. The same hand may be used to remove the sharp guard 10 from the dispenser 40. The lid closure 50 may then be closed by a single hand or finger and the lock holds the lid closure 50 closed.

Figure 5:
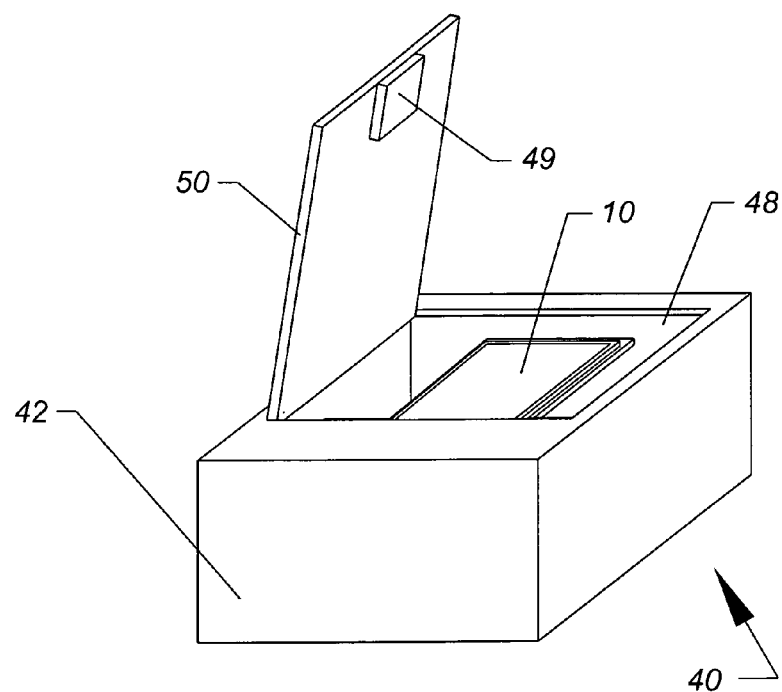
FIG. 5 illustrates an oblique view of another embodiment of a dispenser for sharp guards comprising a single central opening on the top of the dispenser and a one-hand operated spring-loaded lid.

FIG. 5 illustrates another embodiment of the dispenser 40 for sharp guards 10 comprising the case 42, the opening 48, the lid closure 50, a latch or lock 49, and the plurality of undeployed sharp guards 10. In this embodiment, the opening 48 is arrayed generally centrally on a top surface of the case 42. The lid closure 50 is preferably biased open by a spring. The spring may be a leaf spring, a coil spring, or any other type of spring. The latch or lock 49 is operable by simple pressure with a single finger and depression of the lock 49 causes the lid closure 50 to open by stored force in the spring and permits access to the contents of the case 42. The latch or lock 49 is, in an embodiment, a simple molded catch or protrusion that engages with a feature on the case 42 and prevents the lid closure 50 from opening. Depression of the latch or lock 49 causes the catch or protrusion to become disengaged with the case 42 and allows the spring to move the lid closure 50 to the open position. The lid closure 50 may then be closed with a single hand and the latch or lock 49 engages with the case 42 when the lid closure 50 is pushed closed. The stored force to open the lid closure 50 may be generated by methods such as, but not limited to, a spring, a magnet, a motor, hydraulic or pneumatic pressure, and the like.

In an embodiment, the dispenser 40 presents the user with the open sharp guard 10. The medical caregiver places the contaminated sharp 30 against the lower adhesive region 26 and presses the sharp 30 against the fold or hinge area 14. The dispenser 40 causes the protective covers of the upper and lower supports 12, 14 to fold over the sharp 30 under the influence of downward manual pressure and coercion from side compression members on the dispenser 40. The sharp guard 10 finally closes and irreversibly seals over the sharp 30. The disabled sharp 30 and its protective cover or sharp guard 10 are removed from the dispenser 40 and placed in a receptacle. Another sharp guard 10 moves into place to contain another sharp 30. In another embodiment, the closing action for the sharp guard 10 may be derived from an active source such as a motor, pneumatic or hydraulic cylinder, or the like.

Figure 6A:
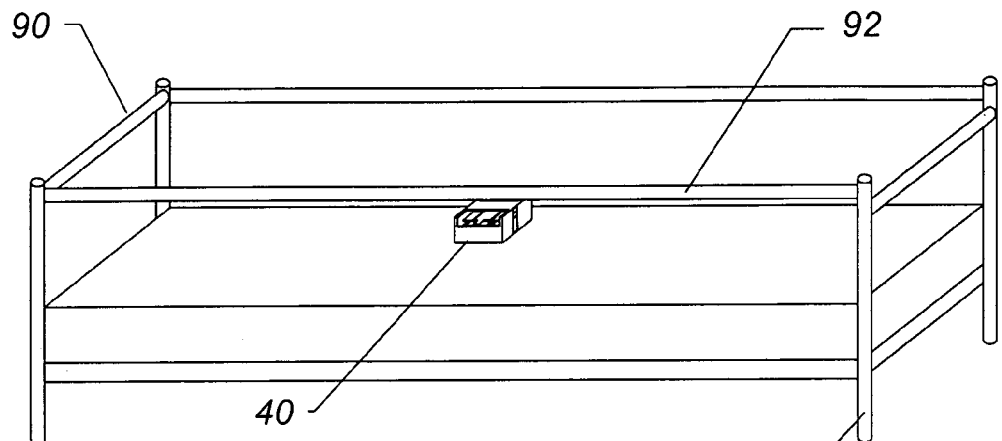
FIG. 6A illustrates an oblique view of a sharp guard dispenser attached to the rail of a hospital bed, according to an embodiment of the invention.

FIG. 6A illustrates a hospital bed 90 comprising a plurality of bed rails 92 and a plurality of bed posts 94. The sharp guard dispenser 40 can be attached to one of the bed rails 92 for easy access by medical personnel.

Figure 6B:
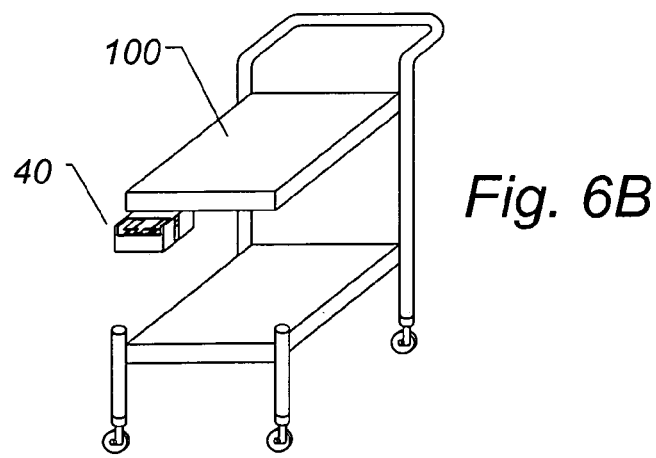
FIG. 6B illustrates an oblique view of the sharp guard dispenser attached to a bed stand, according to an embodiment of the invention.

FIG. 6B illustrates a bed stand 100 with the sharp guard dispenser 40 attached thereto. Attachment to the bed stand 100 is performed by means of a clamp, clip, Velcro, adhesive, or other fastening method. The attachment is reversible in that the dispenser 40 is removed once it is empty and the dispenser 40 can be replaced by one containing at least one sharp guard 10.

Figure 7A:
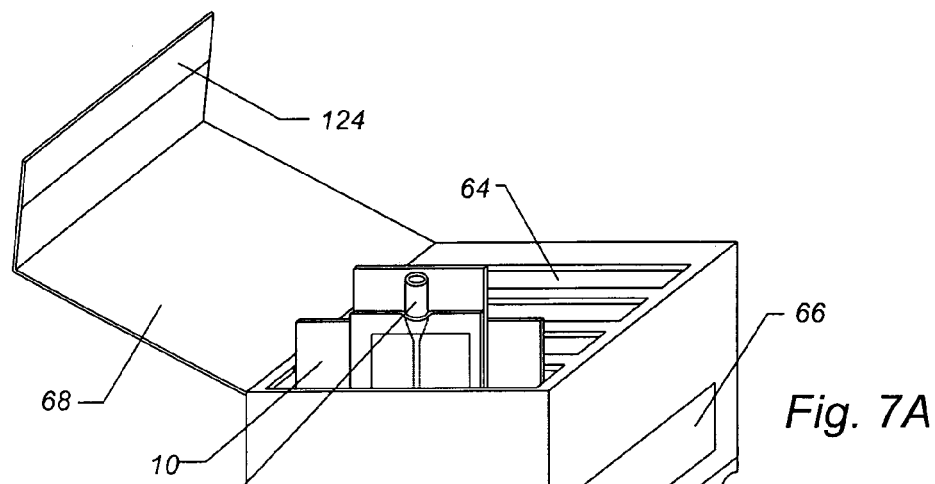
FIG. 7A illustrates an oblique view of the sharp guard receptacle with a sharp guard being inserted, according to an embodiment of the invention.

FIG. 7A illustrates a receptacle 60 for used sharp guards 10, comprising a case 62, a plurality of openings 64, an optional window 66, a bracket or mount 67, and a lid closure 68. The sharp guard 10 is shown comprising the medical sharp object 30. The receptacle 60 is sized to fit sharp guards 10 and used entrapped medical sharps 30.

In an embodiment, the case 62 of the receptacle 60 is fabricated from materials including, but not limited to, polyvinyl chloride, polyethylene, polypropylene, polyester terephthalate (PET), acrylonitrile butadiene styrene (ABS), polystyrene, copolymers of the aforementioned, metal, sealed wood, cardboard, or any other material suitable for a container. The preferred material is PET, cardboard, or polystyrene because of the low manufacturing cost of these materials. Preferred manufacturing methods for the case 42 include, but are not limited to, lamination, blow molding, extrusion, injection molding, or the like. The bracket or mount 67 comprises releasable or non-permanent adhesives, magnets, Velcro, clips, clamps, snaps, bayonet mount, screw mounts, or the like.

In an embodiment, the optional window 66, which can be either open or sealed with transparent polymer, allows the user to visually monitor the contents and fill level.

In another embodiment, the receptacle 60 further comprises a seal 124. In an embodiment, the seal 124 is located on the lid closure 68. When the medical sharps receptacle 60 is full, the user closes the lid 68 and enables the seal 124 to prevent the receptacle 60 from opening. The receptacle 60 is then discarded. By this means, a user cannot attempt to discard a used sharp guard 10 in the full receptacle 60, as the opening 64 is sealed shut.

Figure 7B:
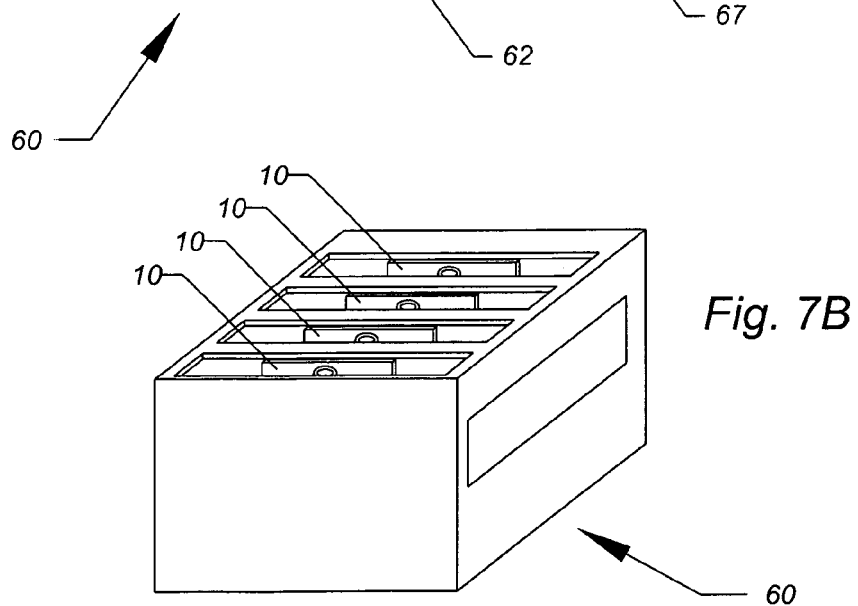
FIG. 7B illustrates an oblique view of the sharp guard receptacle, which has become full and can no longer accept new sharp guards, according to an embodiment of the invention.

FIG. 7B illustrates the receptacle 60 with the sharp guard 10 inserted into every opening 64. Not only can the user see that each opening 64 is filled with the sharp guard 10, but it is impossible to put additional sharp guards 10 into the receptacle 60 because all the openings 64 are obstructed by the sharp guard 10. In an embodiment, the receptacle 60 further comprises an optional permanent adhesive on its interior wall opposite the openings 64. Once the user inserts the sharp guard 10 into the receptacle 60, the adhesive adheres the sharp guard 10 to the wall, and prevents removal of the sharp guard 10.

Referring to FIG. 1C, in another embodiment, the adhesive catalyst 32 promotes bonding between the sharp guard 10 and the adhesive within the receptacle 60 to further prevent removal of the used sharp guard 10 from the receptacle 60.

Figure 8:
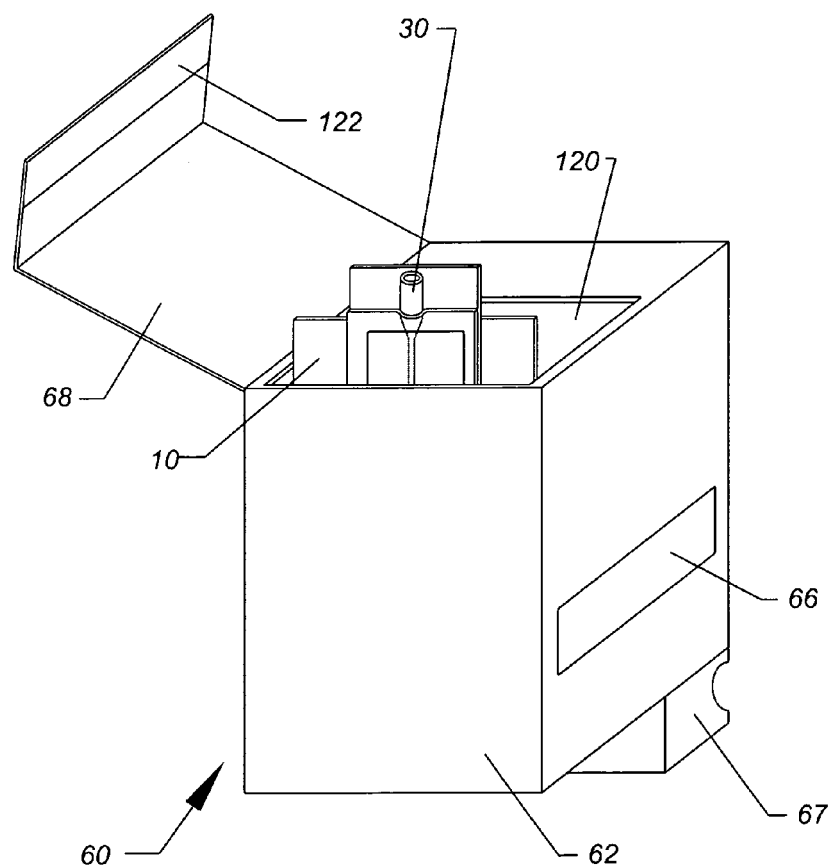
FIG. 8 illustrates an oblique view of another embodiment of a receptacle for sharp guards comprising a single opening and a single area to hold the sharps, according to an embodiment of the invention.

FIG. 8 illustrates another embodiment of the receptacle 60 for sharp guards 10, comprising the case 62, a single opening 120, the window 66, the bracket or mount 67, and the lid closure 68. The lid closure 68 further comprises a latch or lock 122. The sharp guard 10, shown comprising the medical sharp object 30, is being inserted into the opening 120. The window 66 permits viewing of the contents of the receptacle 60 when the lid closure 68 is closed. The case 62 constrains an internal chamber that is accessed by the opening 64 and permits storage of sharp guards 10 with embedded medical sharps 30.

The lid closure 68 is preferably biased open by a spring. The spring may be a leaf spring, a coil spring, or any other type of spring. The latch or lock 122 is operable by simple pressure with a single finger. Depression of the lock 122 causes the lid closure 68 to open by stored force in the spring and permits used sharp guards 10 with embedded sharps 30 to be placed or disposed of within the case 62. Such a latch or lock 122 is, in a preferred embodiment, a simple molded catch or protrusion that engages with a feature on the case 62 and prevents the lid closure 68 from opening. Depression of the latch or lock 122 causes the catch or protrusion to become disengaged with the case 62 and allows the spring to move the lid closure 68 to the open position. The lid closure 68 may then be closed with a single hand and the latch or lock 122 engages with the case 62 when the lid closure 68 is pushed closed. The stored force to open the lid closure 68 may be generated by methods such as, but not limited to, a spring, a magnet, a motor, hydraulic or pneumatic pressure, or the like.

In another embodiment of the receptacle 60, a specialized lid is configured to clamp to the top of a trashcan or standard medical sharps container. The specialized lid is designed to allow the single sharp guard 10 and encased sharp 30 to be inserted into the receptacle 60. The specialized lid prevents overfilling of the receptacle 60 by becoming unable to open when the interior space of the case 62 is full.

In another embodiment, the user can discard the used, employed sharp guard 10 in any standard biohazard waste disposal container.

Figure 9A:
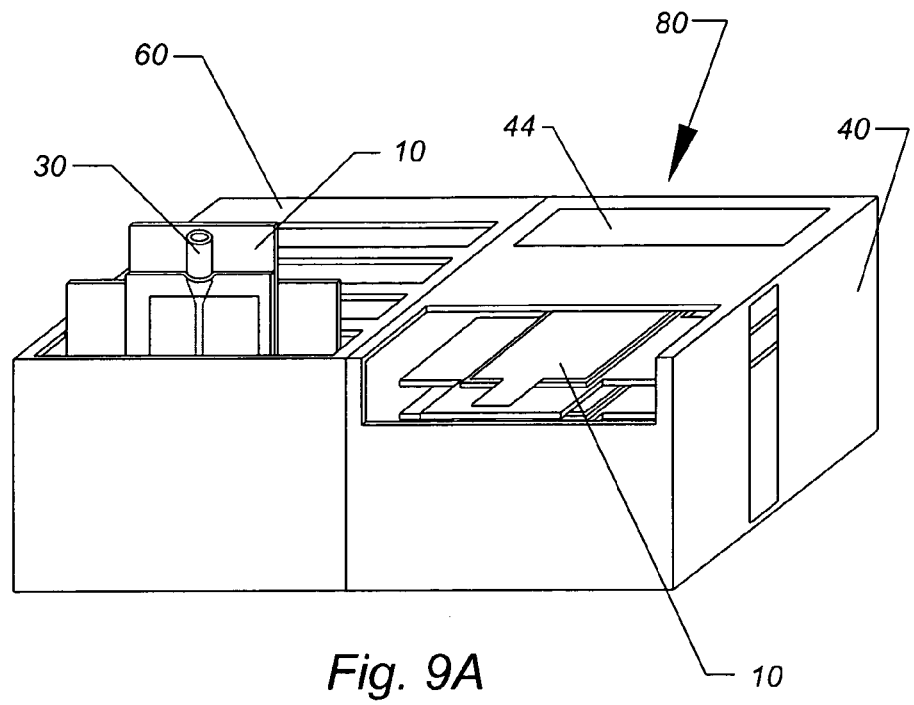
FIG. 9A illustrates a sharp guard delivery system, according to an embodiment of the invention.

FIG. 9A illustrates an oblique view of a sharp guard delivery system 80 comprising the dispenser 40 and the receptacle 60. The dispenser 40 further comprises the plurality of sharp guards 10 and the receptacle 60 is shown with the single used sharp guard 10 being inserted therein. The used sharp guard 10 further comprises the contaminated medical sharp object 30. The delivery system 80 allows for access to sharp guards 10 and a convenient place for storage of used sharp guards 10 so that the medical practitioner or user does not have to travel across the room to dispose of the medical sharp object 30 or sharp guard 10. The unitary design of the sharp guard delivery system 80 occupies minimum space in the medical facility. In an embodiment, the sharp guard delivery system 80 is unitary. In another embodiment, the sharp guard delivery system 80 comprises the dispenser 40 and the receptacle 60 as separate units. In an embodiment, the sharp guard receptacle 60 holds at least as many sharp guards 10 and contaminated medical sharp objects 30 as the dispenser 40 contains when full. The dispenser 40 presents one sharp guard 10 at a time, and upon removal of the presented sharp guard 10, the dispenser 40 presents another sharp guard 10 for use.

Figure 9B:
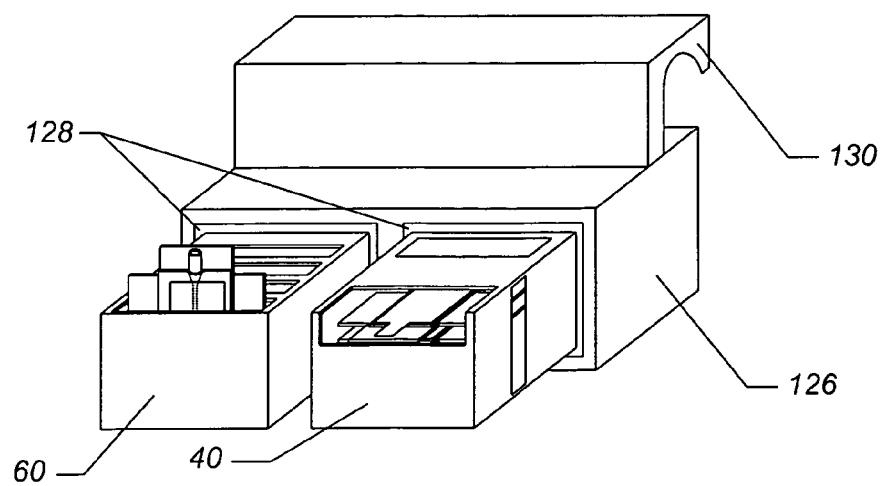
FIG. 9B illustrates another embodiment of a sharp guard delivery system comprising a bracket to hold the dispenser and the receptacle, according to an embodiment of the invention.

FIG. 9B illustrates another embodiment of the sharp guard delivery system 80 comprising the dispenser 40, the receptacle 60, and a bracket 126 to hold the dispenser 40 and the receptacle 60. The bracket 126 further comprises a plurality of recesses 128 to hold the receptacle 60 and the dispenser 40. In addition, the bracket 110 comprises a clamp 130. The clamp 130 is configured to hold the bracket 126 to a wall, bed stand, bed rail, ambulance wall, tabletop, or other hospital or medical location. The clamp 130 is configured in various ways including, but not limited to, a releasable adhesive, Velcro, C-clamp, permanent or electro-magnet, bracket with spring-loaded closure, and the like.

In yet another embodiment of the invention, a bracket is provided that holds the dispenser 40 and the receptacle 60. The bracket allows each of the dispenser 40 and the receptacle 60 to be inserted and locked into place. Removal of the empty dispenser 40 and the full receptacle 60 is accomplished by releasing the lock and removing either the dispenser 40 or the receptacle 60 from the bracket. The bracket may be attached to a bed, bed stand, table, wall or the like and reversibly accept the dispenser 40 and/or the receptacle 60. The bracket may also allow the dispenser 40 to be coupled to a commercially available receptacle.

In an embodiment, this invention comprises the methods of placing a sharp guard 10 or other medical sharps receiver at a location proximate to where it will be used medically, or at the point-of-use. It is preferable that such proximate location is no further than 15 feet from where the sharp 30 is used and, more preferably, the location is less than 5 feet from where the medical sharp is used. Most preferably, such proximate locations is such that the medical professional does not have to move his feet or even turn to reach a sharp guard 10 from where the medical sharp 30 is used on a patient.

The receptacle 60 is preferably located proximate to the patient use of the medical sharp 30. The sharp guard 10 is provided by the dispenser 40 affixed proximate to where the medical sharp 30 is used on the patient. The sterile sharp guard 10 may also be taken from another location and moved to the sterile field where it is available for use immediately after using the sharp 30 on a patient. The person disposing of the sharp 30 entraps the medical sharp 30 within the sharp guard 10 at or near the point-of-use so that the medical sharp 30 is not moved around the room in such a way as it might cut or puncture another person. Once entrapped within the sharp guard 10, the healthcare worker transports the medical sharp 30 to the receptacle 60 where it is safely discarded.

Figure 10:
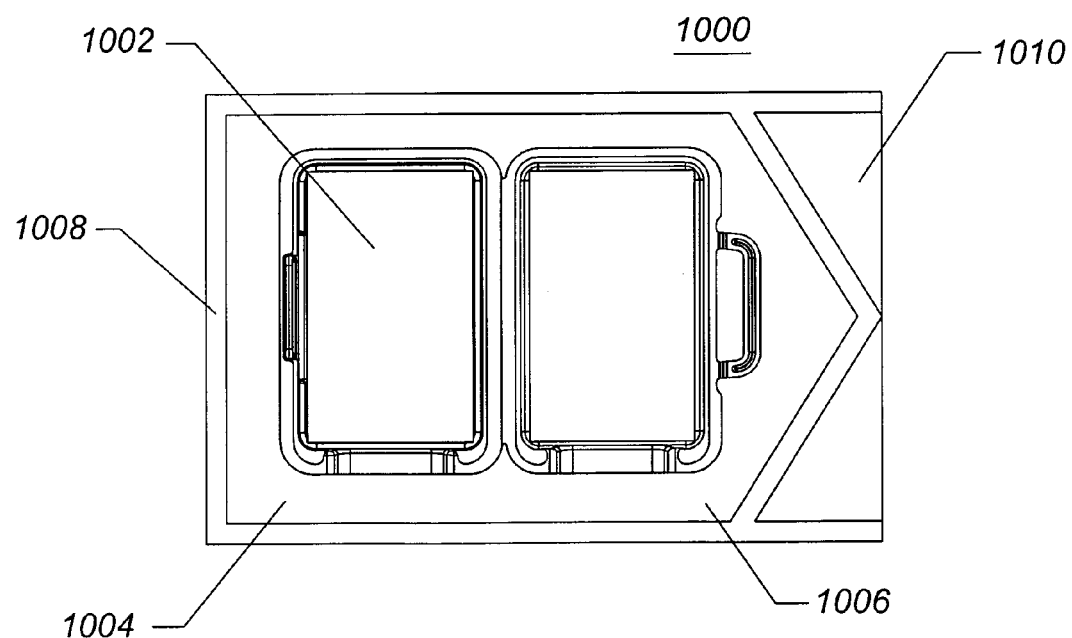
FIG. 10 illustrates an embodiment of the sharp guard in its sterile package, according to an embodiment of the invention.

FIG. 10 illustrates an embodiment of a packaged sharp guard 1000 comprising a sharp guard 1002 enclosed and sealed within its aseptic packaging 1004. The aseptic packaging 1004 comprises a microbe impermeable pouch 1006 closed with a plurality of seals 1008, and further comprising an opening tab 1010.

Referring to FIG. 10, the microbe impermeable pouch 1006 can be fabricated from two layers of material such as, but not limited to, metal foil, polyester, PETG, Tyvek®, and the like. The seals 1008 can be heat seals or they can be integrally formed folds in the pouch 1006. The heat seals 1008 can be created by a heater applying heat and pressure for a period of time sufficient to melt two layers of pouch 1006 or material together. The width of the seals 1008 can range from about 0.05 inches to 1.0 inches and preferably around 0.375 inches. The opening tab 1010 can be an unsealed edge region that permits an operator to separate the material layers and gain enough grip to pull the seals 1008 apart. In an embodiment where gas such as ethylene oxide is used for sterilization, a gas permeable pouch comprising at least one layer fabricated from Tyvek® or similar is beneficial. If radiation sterilization is used, for example gamma irradiation or electron beam irradiation, a dosage of about 25 to 40 kiloGrays (kGray) is generally suitable to provide a sterility assurance level (SAL) of 1 in a million ($10^{-6}$). A second aseptic package (not shown) surrounding the packaged sharp guard system 1000 can increase sterility assurance and improve delivery to the sterile field.

Figure 11A:
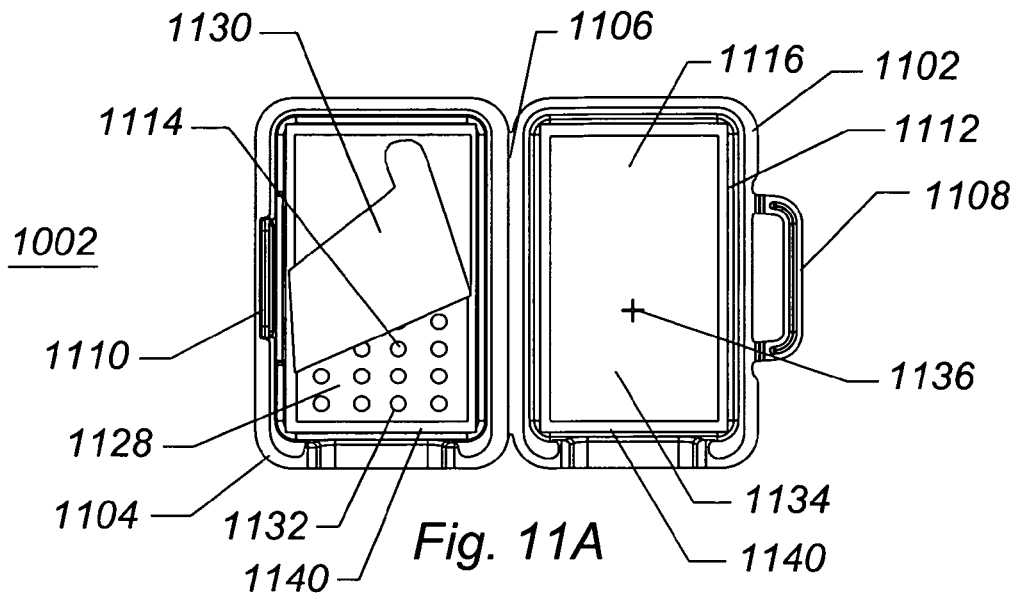
FIG. 11A illustrates a top view of an embodiment of the sharp guard removed from its sterile package in its unfolded configuration, according to an embodiment of the invention.

FIG. 11A illustrates an embodiment of the open sharp guard device 1002, following removal from its aseptic packaging 1004. The sharp guard 1002 comprises a lower shell 1102, an upper shell 1104, a hinge 1106, a latch 1108, a locking detent or latch hook 1110, a puncture resistant liner or inner barrier 1112, a lower foam pad 1116, and an upper foam pad 1114 further comprising an adhesive layer 1128 and a cover strip 1130. The lower foam pad 1116 further comprises an imprinted label 1134 and a needle re-capping station 1136. The sharp guard 1002 further comprises a separate sealing foam or gel 1140.

Referring to FIG. 11A, the sharp guard device 1002 is configured for minimum cost and maximum utility in the medical environment. The upper shell 1104 and the lower shell 1102 can both be affixed to each other by the hinge 1106. The hinge 1106 can be integral to, or separately attached to the upper shell 1104 and the lower shell 1102. The latch hook 1110 can be affixed to, or integral to, the upper shell 1104. The latch 1108 can be integral to, or affixed to, the bottom shell 1102. The latch 1108 can be affixed to the bottom shell 1102 by welding, bonding, hinge pins, fasteners, or the like. The hinge 1106 can be configured as a simple fold, or it can comprise a plurality of folds such as in a "Z" fold. The hinge 1106 can comprise areas of variable thickness to enhance flexibility. The hinge 1106, in a preferred embodiment, can be configured to maintain the upper shell 1104 and the lower shell 1102 flat and stable prior to closure. The hinge 1106, in a preferred embodiment, retains the upper shell 1104 and the lower shell 1102 open and opposed to each other and laying substantially flat against a flat surface, such as a table top or countertop. The hinge 1106 in its flat, open, embodiments allow the sharp guard 1002 to remain highly stable in its open, resting position. In some embodiments, the flat hinge 1106 can be formed by first thermoforming or molding a flat web between the lower shell 1102 and the upper shell 1104. A secondary operation can then be performed to either melt, cut, stamp, or otherwise form a groove or thin area in the web to enhance flexibility and allow the hinge 1106 to lie flat when the upper shell 1104 and the lower shell 1102 are open but still close easily and without resistance.

The exposed surface the upper pad 1114, which can also be termed a foam pad, a pad, a foam block, a block, a space filler, or the like, can comprise a highly aggressive adhesive layer 1128 capable of gripping medical devices embedded therein with a high degree of friction or adhesiveness. The adhesive pad 1128 can further comprise a plurality of holes 1132 that completely penetrate the adhesive layer 1128 to allow fluids to be absorbed by the open cell foam pad 1114. The adhesive layer 1128 can also be termed a film, a pad, an intermediary, or other suitable descriptor. The adhesive layer 1128 can be advantageously provided with a removable cover strip 1130, shown partially pulled up and off the adhesive layer 1128, and fabricated from low friction materials such as polyethylene, polypropylene, PTFE, and the like, wherein the cover strip 1130 can be removed prior to use by the operator. The cover strip 1130 can be fabricated inexpensively with materials such as paper treated, coated, embedded with, sprayed on, or dipped in, silicone release agent, silicone oil, or the like. The low friction treatment of the cover strip 1130 is preferably applied only to one side, the side that contacts the adhesive 1128. The cover strip 1130 can be provided with instructions, labels, and other information to minimize the need for additional instructions within the device packaging and it can be provided with a grip tab for easy grasping and removal. The cover strip 1130 can also be termed a liner.

The lower foam pad 1116 can also be termed a foam pad, a pad, a foam block, a block, a space filler, or the like. The label 1134 can be adhered to or directly imprinted upon the lower foam pad 1116. Processes suitable for printing on open-celled foam are appropriate for this label 1134. Such processes include, but are not limited to, sublimation printing, inkjet printing, silkscreen printing, and the like. The label 1134 can comprise information such as, but not limited to, symbols indicating where to insert the medical sharps, the location of a re-capping station, specifications for the maximum size of medical sharps to be inserted, the orientation of insertion, a region for counting needles, and the like.

The lower shell 1102, the upper shell 1104, the hinge 1106, and, optionally the latch 1108 and the latch hook 1110 can be manufactured from a sheet extrusion of polymer, injection molding, or the like. Sheet extrusion converts thermoplastic pellets or powder into continuous, controlled thickness, rolls of single or multi-layer materials (co-extrusion), which are suited for further processing. The sheets are then re-softened and molded by air pressure or vacuum to define the part's interior and exterior shape in a process called thermoforming, pressure forming, or vacuum forming. Features such as hinges, latches, detents, seals, and the like can all be produced integral to the lower shell 1102, the upper shell 1104, or both.

Figure 11B:
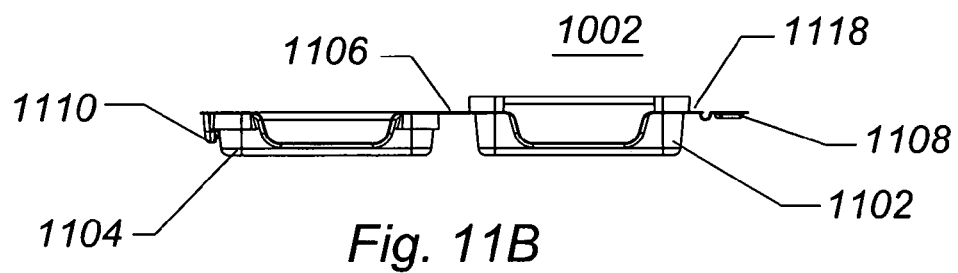
FIG. 11B illustrates a side end view of the open sharp guard of FIG. 11A, according to an embodiment of the invention.

FIG. 11B illustrates a side view of the sharp guard device 1002 as viewed from the end where syringe barrels are inserted. The sharp guard device 1002 comprises the bottom shell 1102, the upper shell 1104, the latch hook 1110, the latch 1108, the hinge 1106, and the latch hinge 1118.

Referring to FIG. 11B, the latch 1108 is affixed to the bottom shell 1102 by the latch hinge 1118. The latch hinge 1118 can be a fatigued region of polymer, it can comprise hinge pins and holes, it can comprise a thin region of polymer, it can comprise a ball and socket, it can comprise an arcuate bend in the polymeric material, it can comprise a "Z" fold, and the like. The hinge 1106 and the latch hook 1110 preferably are fabricated from the same materials as the lower shell 1102 and the upper shell 1104. The bottom shell 1102, the upper shell 1104, the hinge 1106, the latch 1108, and the latch hook 1110 can all be fabricated at the same time using a single process such as, but not limited to, injection molding, thermoforming, vacuum molding, and the like. The bottom shell 1102, the upper shell 1104, the hinge 1106, the latch 1108, and the latch hook 1110 can comprise materials such as glycol modified PET (PETG), PET, polyurethane, polysulfone, PEEK, polyethylene, HDPE, LDPE, polypropylene, and the like. The materials can be co-extruded to generate multi-layer structures or multi-component multi-layer structures. The thickness of the bottom shell 1102 and the top shell 1104 can range between approximately 0.005 inches and 0.125 inches with a preferred range of approximately 0.020 to 0.050 inches.

Figure 11C:
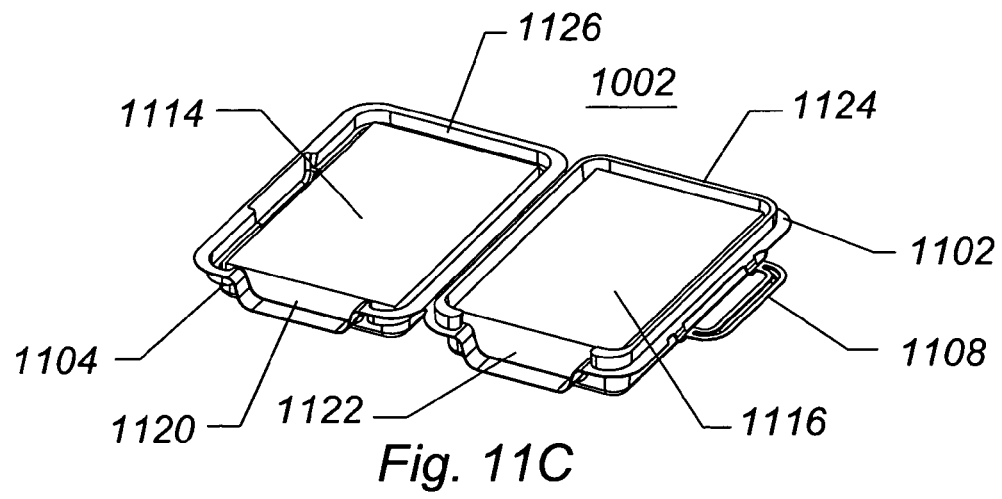
FIG. 11C illustrates an oblique view of the open sharp guard of FIG. 11A, according to an embodiment of the invention.

FIG. 11C illustrates an oblique view of the sharp guard device 1002. The sharp guard 1002 comprises the lower shell 1102, the upper shell 1104, the lower pad 1116, the upper pad 1114, the lower opening 1122, the upper opening 1120, and the latch 1108. The lower shell 1102 further comprises a sealing flange 1124 and the upper shell 1104 further comprises the sealing receiver 1126. The sealing flange 1124 and the sealing receiver 1126 can further comprise snap features that permit a small or substantial degree of tactile closure and locking. The snap features can also provide a degree of audible closure feedback. The sealing flange 1124 can comprise projections (not shown) that engage, mate, and lock with detents in the sealing receiver 1126.

Referring to FIG. 11C, the lower pad 1116 and the upper pad 1114 are inserted into the lower shell 1102 and the upper shell 1104, respectively. The pads 1114 and 1116 can be a slip fit, a press fit, heat welded to, ultrasonically welded to, or adhesively bonded to their respective shell structures 1104 and 1102. The pads 1114 and 1116 are preferably fabricated from memory foam. That is, the pads 1114 and 1116 can be fabricated from foam that has little recovery force. When the foam becomes deformed, it remains deformed with little or no substantial spring-back. Suitable foam structures include those fabricated from polyurethane foam, polycarbonate foam, and the like. Open-cell, closed-cell, and partially open cell foam structures can be suitable for the application. An open-cell structure has at least one surface comprising interconnected cells with open ends to allow any residual biological fluids to coalesce and flow into the interior absorptive layers of the foam. The surface is preferentially slightly tacky with a high coefficient of friction to hold and support medical instrument barrels and handles so that they cannot slide or be pulled from the grip of the foam. The external surface of the foam structure, along all surfaces except the open central area of the top and bottom, is preferably closed-cell so that the foam forms a fluid-tight barrier to liquids contained therein. It is especially beneficial that the foam is closed at the lower opening 1122 and the top opening 1120.

In other embodiments, a separate sealing foam or gel 1140 can be provided at the lower opening 1122 and the upper opening 1120 to further secure the opening area against fluid leakage. The foam pads 1114 and 1116 can also comprise gel materials to form structures with an exceedingly high degree of conformability to inserted medical sharp devices. Exemplary foam for the pads 1114 and 1116 can comprise low-density flexible, polyester urethane foam or similar material with a light compression deflection to conform to individual medical instrument shapes. The density can advantageously range between about 2.0 and 6.0 pounds per cubic foot.

The lower opening 1122 and the upper opening 1120 can be configured such that when the upper shell 1104 is closed against the lower shell 1102, a final opening is configured to fit certain medical devices. In an exemplary embodiment, the composite opening comprising the lower opening 1122 and the upper opening 1120 is just wide and tall enough to pass two 20-cc syringes aligned side by side. In another embodiment, the composite opening can be sized to pass two 10-cc syringes, one 60-cc syringe, two 5-cc syringes, one 20-cc syringe, one 10-cc syringe, one 5-cc syringe, or no syringe at all (no opening). In yet another embodiment, the sharp guard 1002 comprises either an upper opening 1120 or a lower opening 1122, but not both.

In the no opening embodiment, the sealing flange 1124 engages the sealing receiver 1126 around the entire perimeter of the sharp guard device 1002. The sealing flange 1124 can comprise a molded feature in the lower shell 1102 and the sealing receiver 1126 can comprise a molded feature in the upper shell 1104.

In another embodiment, the sealing flange 1124 or the sealing receiver 1126, or both, can further comprise an O-ring or gasket (not shown) fabricated from a soft polymer capable of completely forming a fluid-tight seal between the sealing flange 1124 and the sealing receiver 1126. The gasket (not shown) can be used on the complete sealing embodiment or in embodiments comprising the upper opening 1120 and the lower opening 1122.

Figure 12A:
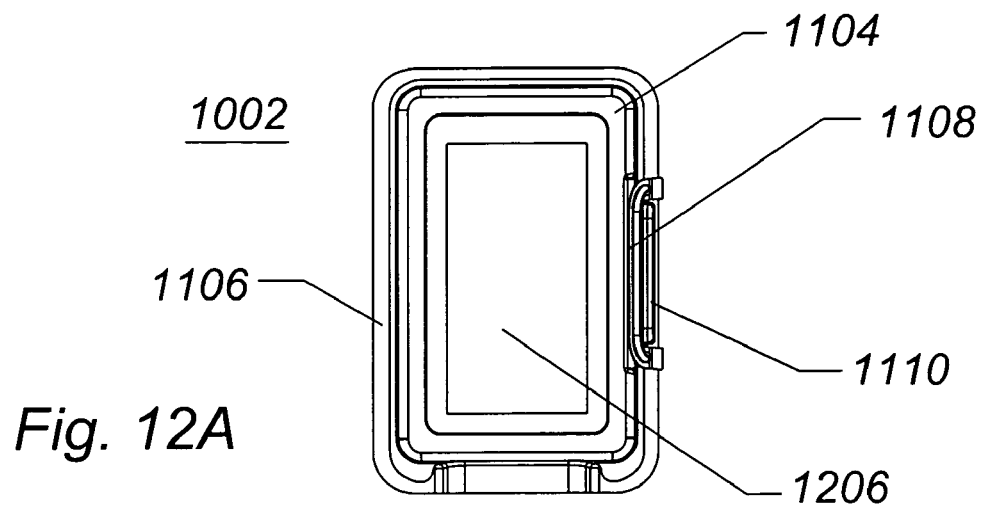
FIG. 12A illustrates a top view of an embodiment of the sharp guard of FIG. 11A following closure, according to an embodiment of the invention.

FIG. 12A illustrates a top view of the sharp guard device 1002 in with the top shell 1104 closed against the bottom shell (not shown). The latch 1108 is closed and irreversibly engaged with the locking detent 1110. The sharp guard 1002 further comprises the hinge 1106 and a label 1206.

Referring to FIG. 12A, the latch 1108 has been rotated about its hinge (not shown) and has been resiliently deformed as it is advanced over a ramp in the locking detent 1110 past a sharp wall (not shown) wherein it resiliently returns to its original unstressed configuration. The latch 1108 is configured such that there is negligible or no opening available between it and the upper shell for an individual to grip, obtain purchase on the latch, or pry the latch 1108 and pull it open, following closure.

Figure 12B:
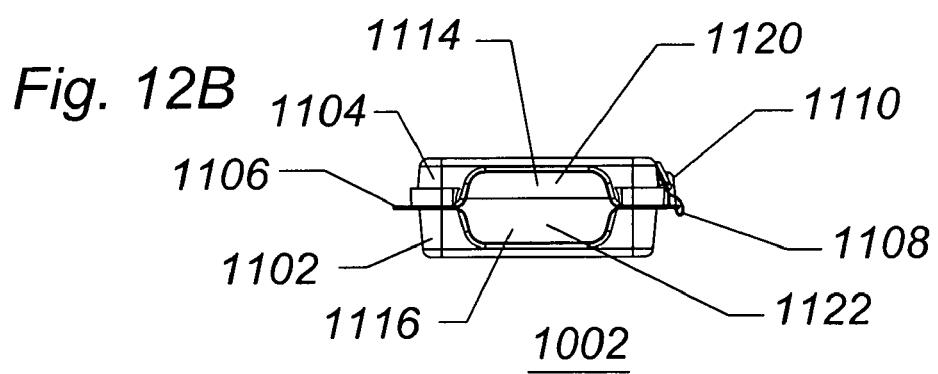
FIG. 12B illustrates an end view of an embodiment of the sharp guard of FIG. 11B following closure, according to an embodiment of the invention.

FIG. 12B illustrates a side view of the closed sharp guard 1002 further comprising the lower shell 1102, the upper shell 1104, the hinge 1106, the lower opening 1122, the upper opening 1120, the latch 1108, the locking detent 1110, the upper foam pad 1114 and the lower foam pad 1116.

Referring to FIG. 12B, the closed sharp guard 1002 is configured to meet all standard requirements for final disposal of medical sharps, prior to being discarded in the red biohazard bags. This includes an inability to re-open and access the disposed medical sharp (not shown), high resistance to puncture, and a fluid-tight seal such that contaminated medical waste does not leak from the sharp guard 1002.

In embodiments wherein the sharp guard 1002 comprises the upper opening 1120, the lower opening 1122, or both, the foam pads 1114 and 1116 come together when the upper shell 1104 closes against the bottom shell 1102. The upper foam pad 1114 compresses and seals against the lower foam pad 1116 to form a fluid tight seal in the window area and, optionally, around the entire periphery of the device 1002.

In some embodiments, the sharp guard 1002 can further comprise an absorbent volume or layer, internally disposed either within the foam pads 1116, 1114, or both, or surrounding the foam pads 1116, 1114. In yet other embodiments, the absorbent material can be dispersed somewhat evenly or unevenly, throughout the foam 1114, 1116. Such absorbent material can comprise methylcellulose, hydrophilic gels or polymers, aerogel, or the like. Materials developed for, and used in the construction of, diapers, absorbent pads, tampons, sanitary pads, and the like can be advantageously used in the sharp guard 1002.

Figure 12C:
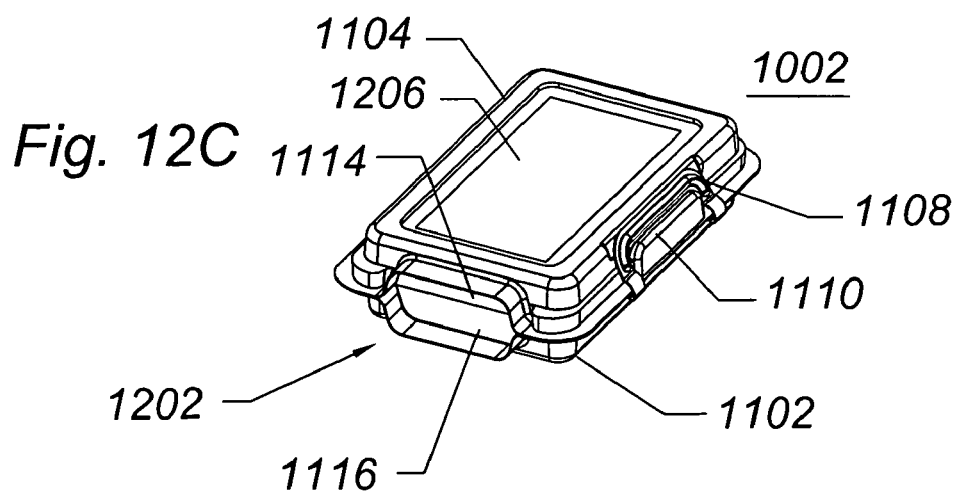
FIG. 12C illustrates an oblique view of an embodiment of the sharp guard of FIG. 11C following closure, according to an embodiment of the invention.

FIG. 12C illustrates an oblique view of the closed sharp guard 1002. The sharp guard 1002 comprises the upper shell 1104, the lower shell 1102, the latch 1108, the locking detent 1110, the opening 1202, the lower foam pad 1116, the upper foam pad 1114, and the label 1206.

Referring to FIG. 12C, the opening 1202 is a composite opening and comprises the upper opening 1120 and the lower opening 1122 of FIG. 12B. The closed sharp guard 1002 is suitable for deposit in a biohazard bag and completely protects individuals from contamination by the used medical sharp devices contained therein.

The sharp guard 1002 can further comprise an inner barrier or liner 1112 (Refer to FIG. 11A) disposed between the lower foam pad 1116 and the lower shell 1102 and, optionally, between the upper foam pad 1114 and the upper shell 1004. The inner barrier or liner 1112, in an exemplary embodiment, can comprise a mat produced from a variety of fibrous materials such as, but not limited to, cotton, cellulose, and synthetic materials including thermoplastics and polyurethanes. The mat layer can range in thickness between about 1/32 and 1/4 inch and preferably between about 1/16 and 1/8 inch. The weight of the mat layer can range between about 1 to 10 ounces per square foot with a preferred range of about 3 to 5 ounces per square foot. The inner barrier or liner 1112 serves as a secondary puncture-resistant layer that complements the shells 1102 and 1104 and provides additional puncture resistance beyond that achievable with the thin polymer outer shells 1102 and 1104. The inner barrier or liner 1112 can be pre-folded and fitted to snugly insert within and entirely, or partially, line the interior surfaces of the lower shell 1102 and the upper shell 1104.

Figure 13A:
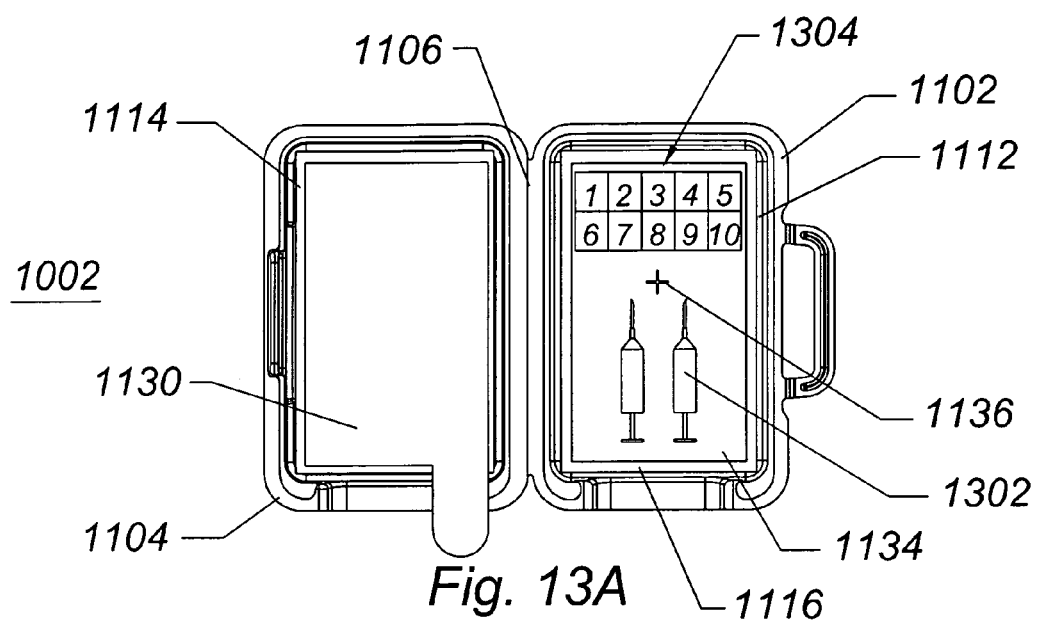
FIG. 13A illustrates an embodiment of a sharp guard foam insert label, according to an embodiment of the invention.

FIG. 13A illustrates an embodiment of a sharp guard 1002 further comprising the lower foam insert label 1134 imprinted on the lower foam block 1116. The sharp guard 1002 comprises the lower shell 1102, the upper shell 1104, the hinge 1106, the upper foam block 1114, the upper adhesive layer (not shown) and the release paper 1130. The sharp guard 1002 further comprises a puncture resistant secondary barrier 1112. The foam insert label 1134 comprises one or more syringe orientation markers 1302, a needle re-capping feature 1136, and a needle counting area 1304.

Referring to FIG. 13A, the foam insert label 1134 can preferably be imprinted on the surface of the lower foam block 1116 but could also be imprinted on the surface of the upper foam block 1114, in an other embodiment. The foam insert label 1134 can be imprinted directly on the foam 1116 or it can be applied as a secondary layer by adhesive or welding means. The foam insert label 1134 can, in another embodiment, be covered by a transparent, or semi-transparent, lower adhesive layer (not shown). Thus the foam insert label 1134 can be sandwiched between foam and adhesive on the bottom, the top, or both parts of the sharp guard 1002. The needle counting area 1304 can be an imprinted pattern of rectangles, triangles, circles, or other geometric designs numbered sequentially to permit the user to embed, place, or insert needles in groups so that they may be more easily counted and accounted for. In the illustrated embodiment, the needle counting area 1304 comprises a series of ten rectangles numbered 1 through 10. The rectangles can be directly imprinted on the foam 1116, in the illustrated embodiment. The user can stick the needle end in the foam or adhere the needle to an adhesive region, or any other suitable means of fixing the needle within the geometric pattern in the desired location. Because the pattern is counted, a user can quickly verify the number of sharp items inside each of the pattern units and organize and account for all the used, contaminated, medical sharps.

Figure 13B:
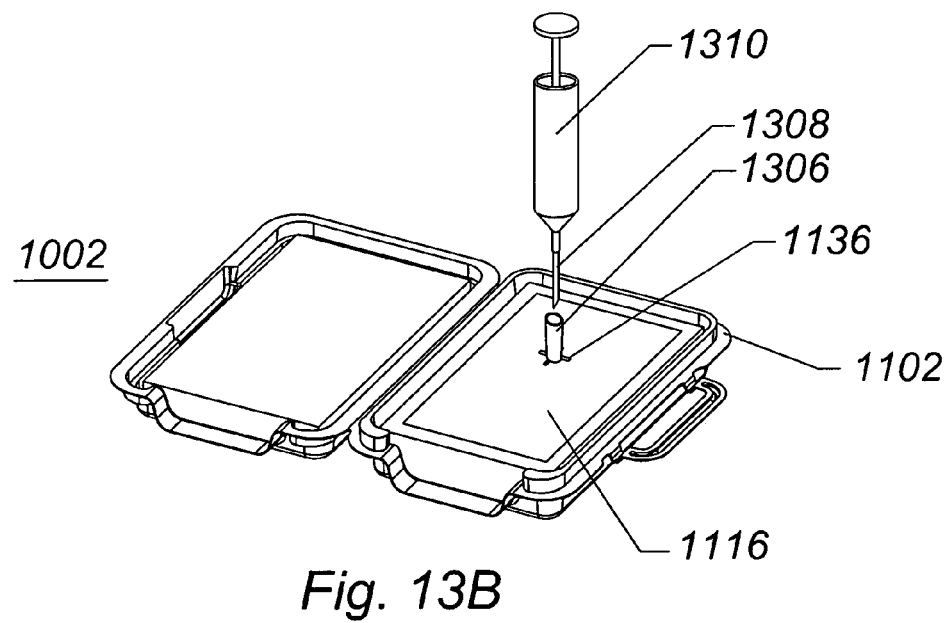
FIG. 13B illustrates an embodiment of a sharp guard further comprising a needle re-capping station being used to re-cap a syringe needle, according to an embodiment of the invention.

FIG. 13B illustrates an embodiment of an open sharp guard 1002 further comprising the needle re-capping station 1136 being used to re-cap a syringe needle 1308. The sharp guard 1002 further comprises the lower foam pad 1116, the lower shell 1102. In the illustrated embodiment, the syringe needle 1308, or hypodermic needle, is affixed to the distal end of a syringe 1310 and a needle cap 1306 is illustrated pushed down into the needle re-capping station 1136 so that its proximal, open end is pointing up.

The lower foam pad 1116 can comprise features suitable for needle re-capping. The needle re-capping feature 1136 can comprise a hole in the foam pad 1116 or it can comprise an X-slit penetrating down into the foam pad 1116, as illustrated. A user can replace the protective cap 1306 over a hypodermic needle that has had its cover removed by inserting the cap closed end into the needle recapping station or feature 1136 with the open end of the cap up. The syringe needle 1308 can then be inserted into the open end of the cap 1306 without the risk of sticking the operator in the hand during the recapping procedure, an all too common occurrence in the medical workplace.

Figure 14A:
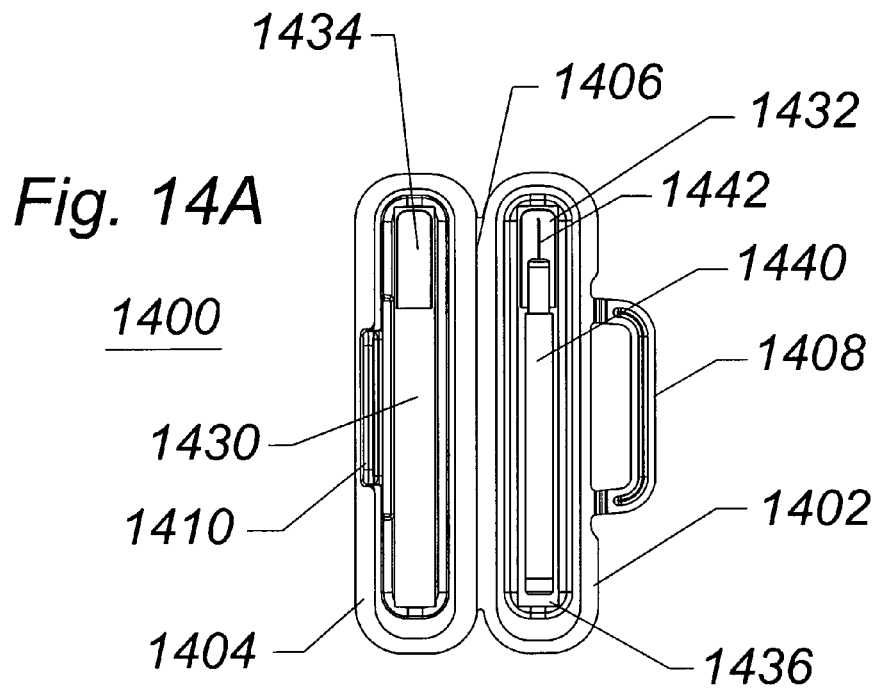
FIG. 14A illustrates an embodiment of the sharp guard wherein the sharp guard forms part of the initial packaging of a dedicated medical sharp, according to an embodiment of the invention.

FIG. 14A illustrates an embodiment of the sharp guard 1400 wherein the sharp guard 1400 forms part of the initial packaging of a dedicated medical sharp 1440 further comprising a sharp needle 1442. The sharp guard 1400 comprises a bottom shell 1402, a top shell 1404, a hinge 1406, a latch 1408, a latch catch 1410, an inner void 1436 configured to accept, hold, and secure the dedicated medical sharp 1440. The sharp guard 1400 can further comprise the optional bottom puncture resistant barrier 1432, the top puncture resistant barrier 1434, or both.

Referring to FIG. 14A, in the illustrated embodiment, the dedicated medical sharp 1440 is an auto-injector used for self-injection of drugs such as, but not limited to, anthrax vaccine, epinephrine, toxin antidotes, insulin, low molecular weight heparin, and the like. The hypodermic needle 1442 can be provided exposed, as illustrated, or it can comprise a closure that serves as an aseptic enclosure (not shown) for the needle 1442. Thus, the sharp guard 1400 can be provided in a sterile pouch or package from which it is removed prior to use, or it can be provided non-sterile but containing a sterilized, aseptically protected dedicated medical sharp 1440. The user removes the dedicated medical sharp 1440 from the sharp shell 1400. The dedicated medical sharp 1440 can be pre-filled with pharmaceutical agents, preferably sterile, or the dedicated medical sharp 1400 can be filled by the user. Following use of the dedicated medical sharp 1440, it is returned to the inner void of the sharp guard 1440, wherein the sharp guard 1440 is then closed and locked to entrap and sequester the used medical sharp 1440 therein.

Figure 14B:
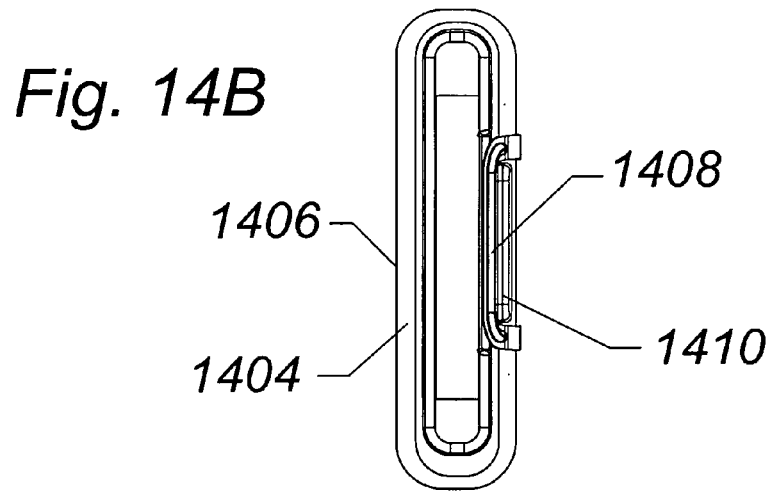
FIG. 14B illustrates an embodiment of the sharp guard following closure around a used, dedicated medical sharp, according to an embodiment of the invention.

FIG. 14B illustrates an embodiment of the sharp guard 1400 following closure around a used, dedicated medical sharp. The sharp guard 1400 in its closed position is illustrated with the upper shell 1404, the hinge 1406, the latch 1408, and the latch catch 1410 showing. The closed sharp guard 1400 is puncture-resistant, locked closed such that it cannot be reasonably re-opened, even if grossly deformed or crushed, and sealed against leakage of liquid enclosed therein. The materials used in fabrication of the dedicated sharp guard 1400 can be the same or similar to those used in fabrication of the more universally applicable sharp guard 1102. The dedicated sharp guard 1400 can further comprise absorbent layers, perimeter seals, multiple locks or latches, foam inserts, adhesive layers, or any of the other features shown in the universal sharp guard 1102. The dedicated sharp guard 1400 can be provided in a single pack, as illustrated, or it can be provided in multiples such as two to a package, three to a package, or any other convenient number. The dedicated sharp guard 1400, in some multiple device embodiments, can have individual closure means or it can have a single closure to seal the unit after all of the plurality of devices have been returned to their proper storage location. In the multiple unit configuration or embodiments, for example, a person might use four insulin syringes in a day and keep the container open until the fourth unit at the end of the day, has been returned to its form fitting void within the sharp guard 1400. Following return of the fourth insulin syringe, the lid can be closed, sealed and locked pending final disposal with other hazardous waste.

Figure 15:
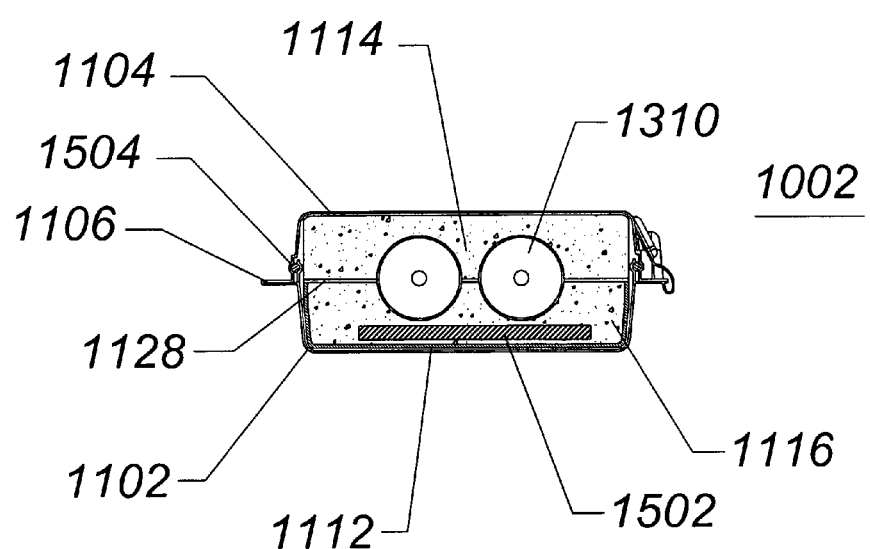
FIG. 15 illustrates a cross-sectional view of a sharp guard further comprising an absorbent pad and a seal gasket around the perimeter, according to an embodiment of the invention.

FIG. 15 illustrates a lateral cross-sectional view of a closed sharp guard 1002 further comprising an absorbent region or pad 1502 and a seal gasket 1504 around the perimeter. The sharp guard 1002 also comprises the lower shell 1102, the upper shell 1104, the hinge 1106, the adhesive layer 1128, the upper foam block 1114, and the lower foam block 1116. Further illustrated is a plurality of syringes 1310 inserted into the sharp guard 1002.

Referring to FIG. 15, the seal gasket 1504 can be affixed to the lower shell 1102 or the upper shell 1104. A second, or more, seal gasket 1504 can be comprised by the upper shell 1104, the lower shell 1102, or both, for additional insurance against fluid leakage from the closed sharp guard 1002. The seal gasket 1504 can comprise a round, rectangular, triangular, or other suitable geometric shape, in cross-section. The seal gasket 1504 can ride within a detent in the upper shell 1104 or the lower shell 1102 and it can further seal within a detent on the complementary shell surface to provide a tactile sense of closure and a reduced risk of re-opening. The seal gasket 1504 can comprise materials such as, but not limited to, silicone elastomer, latex rubber, gel, closed-cell polyurethane or polyethylene foam, polyurethane, thermoplastic elastomer, or the like. The material hardness can range between 5 A and 90 A with a preferred range of 5 A to 60 A. The seal gasket 1504 or its mating surface on either the upper shell 1104 or the lower shell 1102 can further comprise an adhesive to provide additional gap filling and resistance against re-opening. The seal gasket 1504 can completely surround the perimeter of the lower shell 1102, the upper shell 1104, or both. In other embodiments, the seal gasket 1504 can partially surround the perimeter of the upper shell 1104, the lower shell 1102, or both. For example, in FIG. 11C, the seal gasket would not span the openings 1120 and 1122.

The absorbent pad 1502 can be a layer embedded within the lower foam block 1116, the upper foam block 1114, or both. In other embodiments, the absorbent pad 1502 can be configured as a surround layer that parallels the interior walls of the lower shell 1102, the upper shell 1104, or both. The absorbent pad 1502 can be embedded within the foam, as illustrated, or it can be trapped between the upper foam 1114 and the upper shell 1104 or the lower foam 1116 and the lower shell 1102. In yet other embodiments, the absorbent pad 1502 can comprise a plurality of small cells or volumes embedded or dispersed within the foam 1114 and 1116. In another embodiment, the foam 1114, 1116, or both, can comprise widely disseminated or disperse micro-volumes of absorbent material within their structures. The material comprised by the absorbent pad 1502 can include materials such as, but not limited to, sugar, cellulose, sponge, methyl cellulose, hydrophilic hydrogel, kitty litter, or the like. The absorbent layer 1502 can function to receive and store liquids shed from an entrapped, contaminated sharp and maintain those liquids within the sharp guard 1002 prior to destruction.

Application of the sharp guard system and methods reduces the risk that a medical caregiver will use a hypodermic needle, scalpel, or the like on a patient, turn around and accidentally stab a co-worker while trying to put the sharp into its receptacle. Such a scenario is particular disadvantageous when the patient is a vector for highly pathogenic organisms such as those for hepatitis, human immunodeficiency virus (HIV), and the like. The sharp guard system is universal and does not require that each individual sharp is specially designed to retract or self-blunt. The sharp guards and the methods of using the sharp guards reduce the risk of an inadvertent contamination in the medical environment.

The present invention may be embodied in other specific forms without departing from its spirit or essential characteristics. For example, the sharp guard can, instead, be configured as a single monolithic slab of gel material that entraps the sharp and hardens to embed the sharp. The sharp guard receptacle and dispenser may also be configured to accept such hardenable gel sharp guards. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. An apparatus adapted for entrapment and disposal of contaminated medical sharps comprising:
   a shell having an upper portion and a lower portion, wherein the shell comprises a first, open position and a second, closed position a lip extending substantially around an entire perimeter of at least one of the lower portion and the upper portion;
   a pre-defined hinge connecting the upper portion to the lower portion;
   wherein an inside surface of the lip comprises a sealing flange, the sealing flange substantially extending inside a sealing receiver of at least one of the upper portion and the lower portion, wherein the sealing flange is adapted to prevent a contaminated medical sharp from puncturing across an interface between the upper portion and the lower portion of the closed shell;
   an opening located along an edge of at least one of the upper portion and the lower portion defining a break in the sealing flange, the opening configured to allow a medical sharp to project out of the shell when the shell is closed;
   a first pad affixed to an inside surface of the lower portion, the first pad comprising a first gap-filling deformable layer disposed within the inside surface of the lower portion;
   a sealing foam or gel configured to prevent fluid leakage through the opening when the shell is closed around used medical sharps, having random cross-sectional shapes, projecting through the opening; and
   wherein the first pad further comprises a first adhesive layer.

2. The apparatus of claim 1 wherein the pad further comprises absorbent material.

3. The apparatus of claim 1 further comprising a second pad affixed to an inside surface of the upper portion.

4. The apparatus of claim 3 wherein the second pad further comprises a second adhesive layer.

5. The apparatus of claim 3 wherein the second pad further comprises an absorbent material.

6. The apparatus of claim 1 further comprising a cover strip over the first adhesive layer, wherein the cover strip comprises a pull tab.

7. The apparatus of claim 1 further comprising a non-re-openable, irreversible lock to maintain closure of the shell.

8. The apparatus of claim 1 further comprising a secondary puncture resistant barrier inside the shell.

9. The apparatus of claim 1 further comprising a gasket to seal the perimeter of the upper and lower shell.

10. The apparatus of claim 1 wherein the lower gap-filling foam pad is imprinted with a label.

11. The apparatus of claim 1 wherein the lower gap-filling foam pad further comprises a needle counting area.

12. The apparatus of claim 1 wherein the lower gap filling foam pad comprises a needle re-capping station.

13. The apparatus of claim 1 further comprising a second pad affixed to an inside surface of the upper portion, wherein the first pad compresses and seals against the second pad to form a fluid tight seal at the opening when the shell is closed.

14. An apparatus adapted for entrapment and disposal of contaminated medical sharps comprising:
   a substantially rigid shell having an upper portion and a lower portion, wherein the upper portion comprises a top surface and four sides and the lower portion comprises a bottom surface and four sides, further wherein the top surface and at least three of the four sides on the upper portion and the bottom surface and at least three of the four sides on the lower portion comprise an exterior that is puncture-resistant to medical sharps, wherein the shell comprises a first, open position and a second, closed position; a lip extending substantially around an entire perimeter of at least one of the lower portion and the upper portion;

a pre-defined hinge connecting the upper portion to the lower portion;

wherein an inside surface of the lip comprises a sealing flange, the sealing flange substantially extending inside a sealing receiver of at least one of the upper portion and the lower portion, wherein the sealing flange is adapted to prevent a contaminated medical sharp from puncturing across an interface between the upper portion and the lower portion of the closed shell;

an opening located along an edge of at least one of the upper portion and the lower portion defining a break in the sealing flange, the opening configured to allow a medical sharp to project out of the shell when the shell is closed;

a first pad affixed to an inside surface of the lower portion, the first pad comprising a first gap-filling deformable layer disposed within the inside surface of the lower portion;

a layer affixed to the inside surface of the lower portion configured to form a fluid tight seal when the shell is closed; and a sealing foam or gel configured to prevent fluid leakage through the opening when the shell is closed around used medical sharps, having random cross-sectional shapes, projecting through the opening.

15. The apparatus of claim 14 further comprising a non-re-openable, irreversible lock to maintain closure of the shell.

* * * * *